US008219412B2

(12) United States Patent
Kost et al.

(10) Patent No.: US 8,219,412 B2
(45) Date of Patent: Jul. 10, 2012

(54) ARCHITECTURE FOR ORCHESTRATING PROMOTIONAL SERVICES

(75) Inventors: Cecil Kost, Chapel Hill, NC (US);
Timothy Chrobuck, Seattle, WA (US);
David V Tovrea, Lake Stevens, WA (US); Scott M King, Issaquah, WA (US); Steven E Singer, Woodinville, WA (US); Mark Gleason, Oak Park, IL (US)

(73) Assignee: Skyscape.com, Inc., Marlborough, MA (US)

( * ) Notice: Subject to any disclaimer, the term of this patent is extended or adjusted under 35 U.S.C. 154(b) by 2215 days.

(21) Appl. No.: 10/850,654

(22) Filed: May 21, 2004

(65) Prior Publication Data

US 2004/0236607 A1 Nov. 25, 2004

Related U.S. Application Data

(60) Provisional application No. 60/472,950, filed on May 22, 2003, provisional application No. 60/573,234, filed on May 21, 2004.

(51) Int. Cl.
*G06Q 10/00* (2012.01)
*G06Q 50/00* (2012.01)
(52) U.S. Cl. ............................................... 705/2; 705/3
(58) Field of Classification Search .................. 705/2–3
See application file for complete search history.

(56) References Cited

U.S. PATENT DOCUMENTS

| 5,845,255 | A | * | 12/1998 | Mayaud | 705/3 |
| 2002/0032582 | A1 | * | 3/2002 | Feeney et al. | 705/2 |
| 2002/0065683 | A1 | * | 5/2002 | Pham et al. | 705/2 |

OTHER PUBLICATIONS

SamplesMD, Business Plan.
SamplesMD, Presentation Slides.
SamplesMD, SamplesMD Application.
SamplesMD, "A Partner for Growth with the Pharmaceutical Industry."

* cited by examiner

*Primary Examiner* — Luke Gilligan
*Assistant Examiner* — Joseph Burgess
(74) *Attorney, Agent, or Firm* — Christensen O'Connor Johnson Kindness PLLC

(57) ABSTRACT

The promotional orchestration engine includes a services engine that provides transactional responses to a user's request, such as informational results being returned to the user or request for further actions that will be forwarded. An analysis engine stores data and provides tactical and strategic level analysis. The analysis engine uses transactional data generated by the services engine to abstract knowledge and consolidate and aggregate such information. The learning engine is a mechanism by which the promotional orchestration engine adapts itself to changing conditions. The learning engine preferably customizes various components of the services engine and components of the analysis engine. The learning engine causes the services engine to present different information over time so as to keep the system fresh. From a user's standpoint, the learning engine allows components of the services engine to be personalized to the particular user.

40 Claims, 19 Drawing Sheets

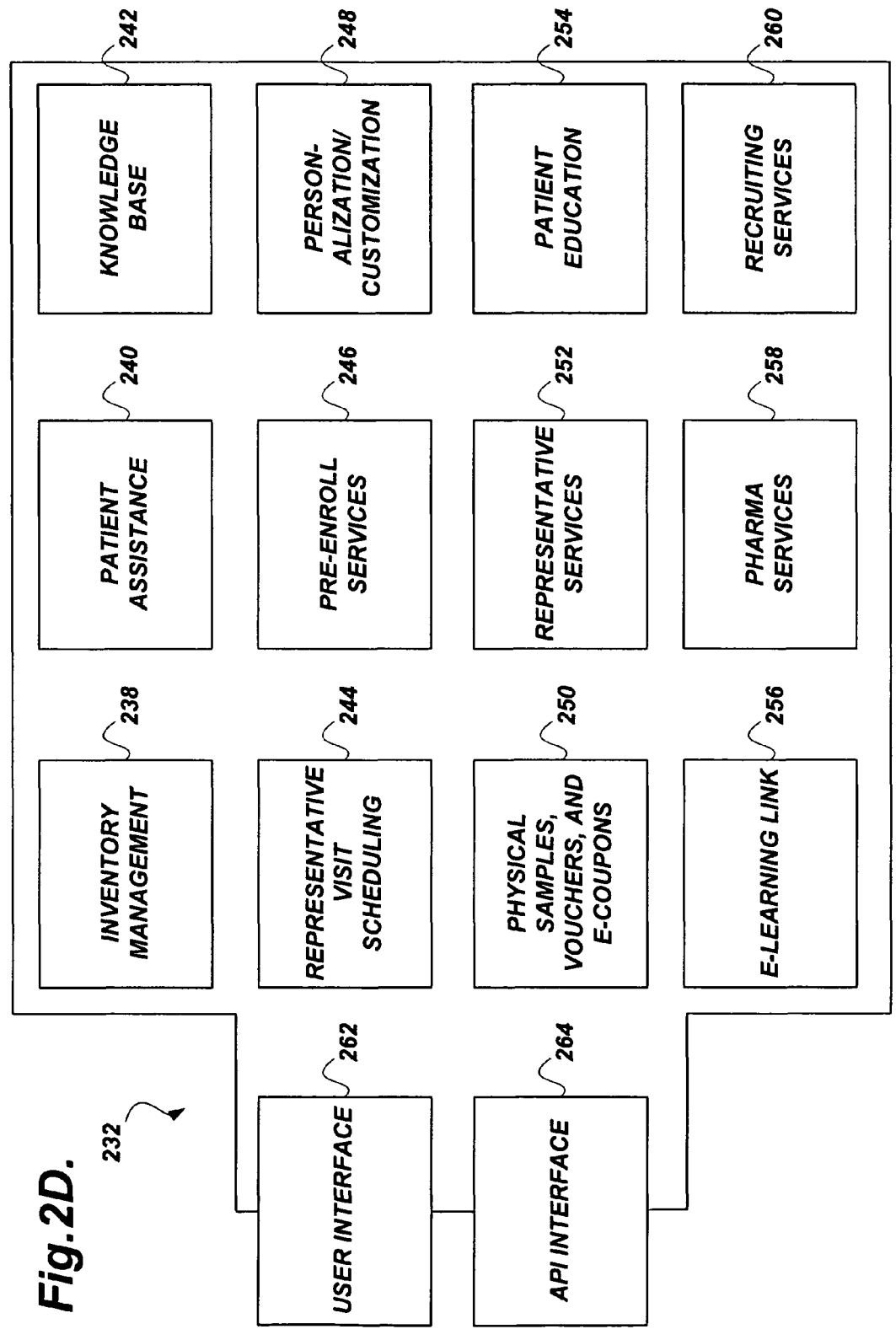

ARCHITECTURE FOR ORCHESTRATING PROMOTIONAL SERVICES

CROSS-REFERENCE TO RELATED APPLICATIONS

This application claims the benefit of U.S. Provisional Application No. 60/472,950, filed May 22, 2003, entitled "PROMOTIONAL TECHNOLOGY ARCHITECTURE," and U.S. Provisional Application No. 60/573,234, filed May 21, 2004, entitled "RULES PROCESSOR," which are incorporated herein by reference.

FIELD OF THE INVENTION

The present invention relates generally to an architecture for orchestrating drug sample distribution, and more particularly, to the design of software relating to drug sample promotion incorporating protocols and means for expansion and interfacing with other systems.

BACKGROUND OF THE INVENTION

After the FDA has approved a drug, a pharmaceutical company promotes the drug the old-fashioned way using face-to-face (personal) selling. Sales representatives of the pharmaceutical company visit one or more prescribers, leave behind drug samples of the drug, and hope that the prescribers will prescribe these drug samples to their patients. As the costs of personal selling have risen, the utilization of sales representatives has changed. With the proliferation of networking technology, many prescribers are members of online communities where promotion and distribution of drug samples can be accomplished without the use of sales representatives.

A drug sample fulfillment platform developed by Med-Manage Systems, Inc., is a system for facilitating the distribution of drug samples with/without the use of sales representatives. The drug sample fulfillment platform is tailored based on the brand rules established by the brand manager for each drug. Using the drug sample fulfillment platform, the brand manager can select which prescribers are authorized to order the drug sample of a brand via a fulfillment platform and the services provided thereon, the forms of drug samples they can access, and the drug sample quantity and delivery method. The drug sample fulfillment platform can be configured to allow a prescriber to request physical samples delivered via common carrier. Requests for such physical samples are electronically communicated (including facsimile communications) to the pharmaceutical company designated fulfillment vendors that pick, pack, and ship physical samples to the requesting prescriber's office. Using this method, prescribers no longer need to rely on sales representatives to deliver physical samples.

To obtain either physical samples or pre-printed vouchers, the prescriber prints one or more order form from a drug sample Web site, signs the order forms, and faxes them a designated fulfillment vendor. The pharmaceutical company specifies a fulfillment vendor (whose fax number is printed on the order form) to which the prescriber faxes the signed order form to obtain physical samples and/or pre-printed vouchers as applicable. While the drug sample fulfillment platform has helped to control the rising costs of personal selling, much of its functionality requires manual work done by hand. For example, the prescriber has to print, sign, and fax an order form for drug samples to a fulfillment vendor. Thus, there is a need for an architecture to orchestrate drug sample distribution while avoiding or reducing the foregoing and other problems.

SUMMARY OF THE INVENTION

In accordance with this invention, a system and method for promoting pharmaceutical drugs is provided. The system form of the invention includes a system for promoting pharmaceutical drugs, which comprises a computer-implemented drug closet for a prescriber. The computer-implemented drug closet displays a number of drug samples available to the prescriber to distribute to a patient. The system further includes a promotional orchestration engine for responding to a request by the prescriber to distribute a drug sample to the patient via the computer-implemented drug closet. The promotional orchestration engine replenishes the number of drug samples in the computer-implemented drug closet according to a set of rules for distributing drug samples to the prescriber. The system further comprises recruiting Web services for executing the set of rules to discover the prescriber as a candidate for prescribing drug samples. The Web services is capable of interacting with the prescriber when the prescriber is logged on to an on-line portal to recruit the prescriber to order the drug samples. The system further comprises a computer-implemented drug closet for a health plan. The computer-implemented drug closet includes drug samples, information, and supplies. The system further comprises an electronic voucher that is generated when the prescriber selects a drug sample from his computer-implemented drug closet to provide to the patient, the electronic voucher being automatically sent to a pharmacy for processing so as to distribute the drug sample to the patient. The system further comprises a customization component for customizing the drug samples in the computer-implemented drug closet depending on the preferences and the behaviors of the prescriber over time in using the computer-implemented drug closet.

In accordance with further aspects of this invention, the system form of the invention includes a system for orchestrating drug sample distribution, which comprises a services engine for fulfilling transaction requests by a prescriber to access services. The system further includes an analysis engine for executing a set of rules associated with a service requested by the prescriber. The set of rules defines whether the prescriber can prescribe a particular drug sample, its dosage, and its form. The system yet further includes a learning engine for adapting the services in the services engine and the set of rules in the analysis engine for customizing information associated with services accessed by the prescriber so that the information appears as if it were personalized to the prescriber.

In accordance with further aspects of this invention, the method form of the invention comprises a method for orchestrating a drug sample promotional campaign, which includes receiving a request by a user to access a service. The method further includes recording the request by an analysis engine. The analysis engine determines a set of rules for governing the service as requested by the user. The method yet further includes adapting a promotional orchestration engine to respond to the behaviors and preferences of the user. The method further also includes determining the set of rules as interactive rules when the request is by a prescriber for samples or e-samples. The method further includes returning a quantity of allowable number of drug samples as a response to the request by the prescriber when the set of rules are interactive rules. The method further includes determining the set of rules as batch rules when an interval of time has expired. The method additionally includes customizing a user interface based on the behaviors and preferences of the prescriber when the set of rules are batch rules.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2D is a block diagram illustrating pieces of a services engine, according to one embodiment of the present invention;

DETAILED DESCRIPTION OF THE PREFERRED EMBODIMENT

Figure 1:
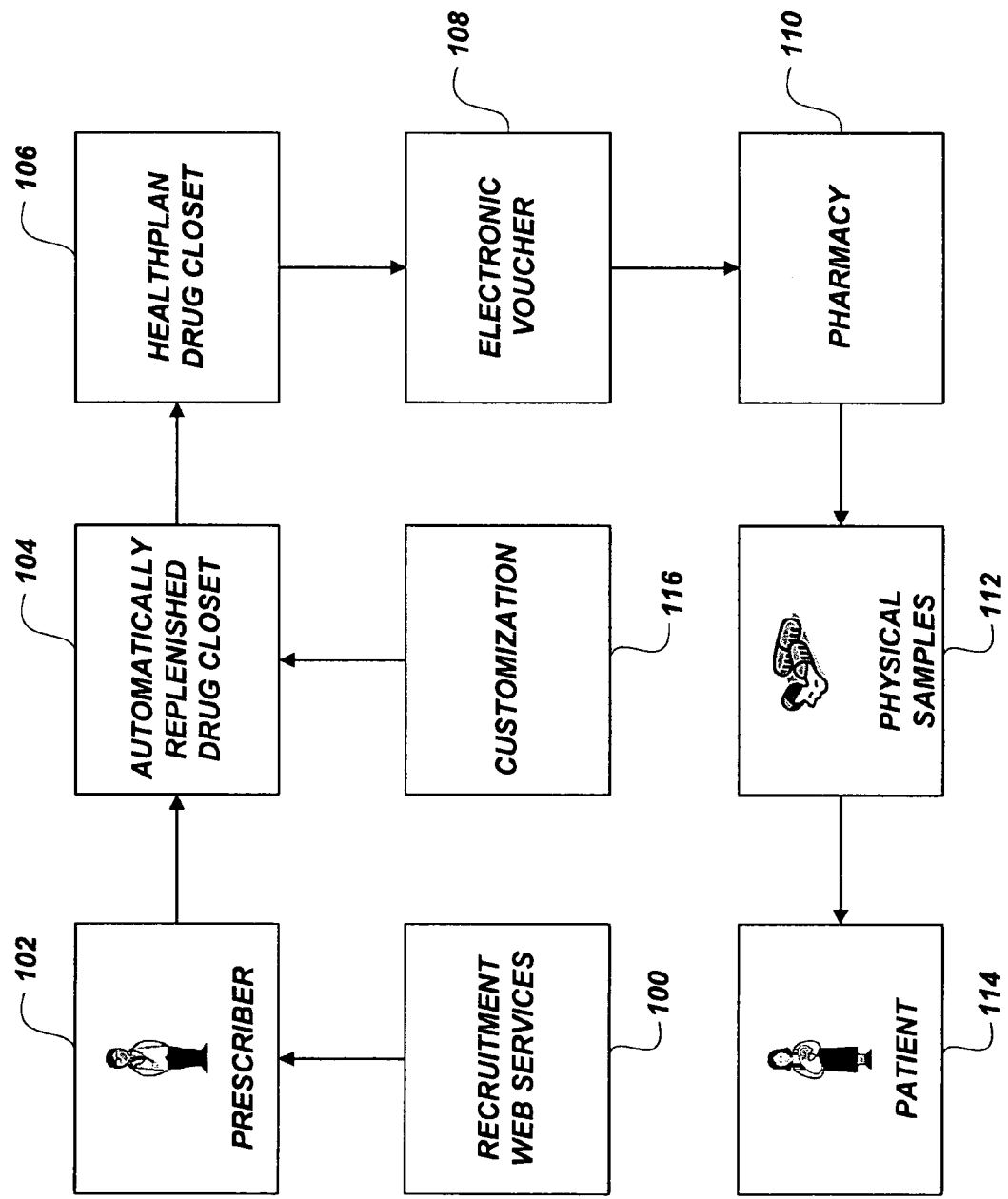
FIG. 1 is a block diagram illustrating pieces of a system for promoting drug samples, according to one embodiment of the present invention.

FIG. 1 illustrates a prescriber 102 who is a licensed professional authorized to prescribe medications, such as physicians, physician assistants, certified registered nurse practitioners, advanced registered nurse practitioners, and so on. Recruitment Web services 100 are a modular collection of Web protocol-based applications that are composed by various embodiments of the present invention to provide discovery and selectivity of a number of prescribers over the Internet to participate in a drug sample distribution campaign. The prescriber 102 may be a member of one or more prescriber-oriented online portals or is identifiable by a prescriber's practice management software running on a computer system in the prescriber's office with access to the Internet. The recruitment Web services 100 select the prescriber 102 by a process of excluding or including based on criteria defined by a pharmaceutical company ("pharma"). These criteria include physician identifier numbers (e.g., state license number, DEA number, and so on), medical practice, specialty, therapeutic class to which drug samples belong, prescribing volume, and past prescribing behavior of the prescriber 102. The term "samples" means the inclusion of live samples, physical samples, printed vouchers, coupons, electronic coupons (e-coupons), and so on.

Once the recruitment Web services 100 select the prescriber 102, the prescriber 102 has access to an automatically replenished drug closet 104 to view drugs or drug samples that are available to him for prescribing to a patient 114. The automatically replenished drug closet 104 resides virtually on the prescriber's practice management software or on a personalized Web page at a pharmaceutical company or prescriber-oriented online portal. Rules are provided by the pharma and are executed or customized over time to determine whether the drug closet 104 should be replenished. Suppose the prescriber 102 distributes to the patient 114 a certain quantity of drug samples. Various embodiments of the present invention can track such prescribed quantity of drug samples so as to automatically replenish the drug closet 104 for the prescriber 102. This automatic replenishment of drug samples frees the prescriber 102 from having to manually keep track of drug samples that are available to him at any point in time. This facilitates and promotes the ability of the prescriber 102 to distribute various drug samples with more regularity. The drug closet 104 is built virtually around a particular prescriber, such as the prescriber 102.

Health plan drug closet 106 is built around a particular health plan that has a preference for a set of pharmaceutical products. This is known as a drug formulary. The drug formulary defines pharmaceutical products that are approved for patients belonging to a particular health plan and are paid for by the health plan less a co-payment by the patient. The health plan drug closet 106 offers preferred pharmaceutical products for the prescriber 102, the patient 114, and a pharmacy 110 so as to ensure health plan compliance and lower cost to the health care system and reduction in errors at the pharmacy 110. To provide samples via a pharmacy, the prescriber 102 preferably selects a drug sample from the drug closet 104. Such selection is automatically transferred to the pharmacy 110 via an electronic voucher 108. The electronic voucher 108 is an organized scheme of data that includes the prescriber's 102 identity, such as his DEA number; the patient's name; and an electronic authorization and authentication. The electronic voucher 108 uses the electronic prescribing system (such as, SureScripts, NDC, and so on) to transmit the prescribed sample information to a specifically selected pharmacy 110 for processing and distributing physical samples 112 to the patient 114. Various embodiments of the present invention observe the preferences of the prescriber 102 and his behaviors to customize his drug closet 104. This is accomplished using a customization component 116.

Figure 2A:
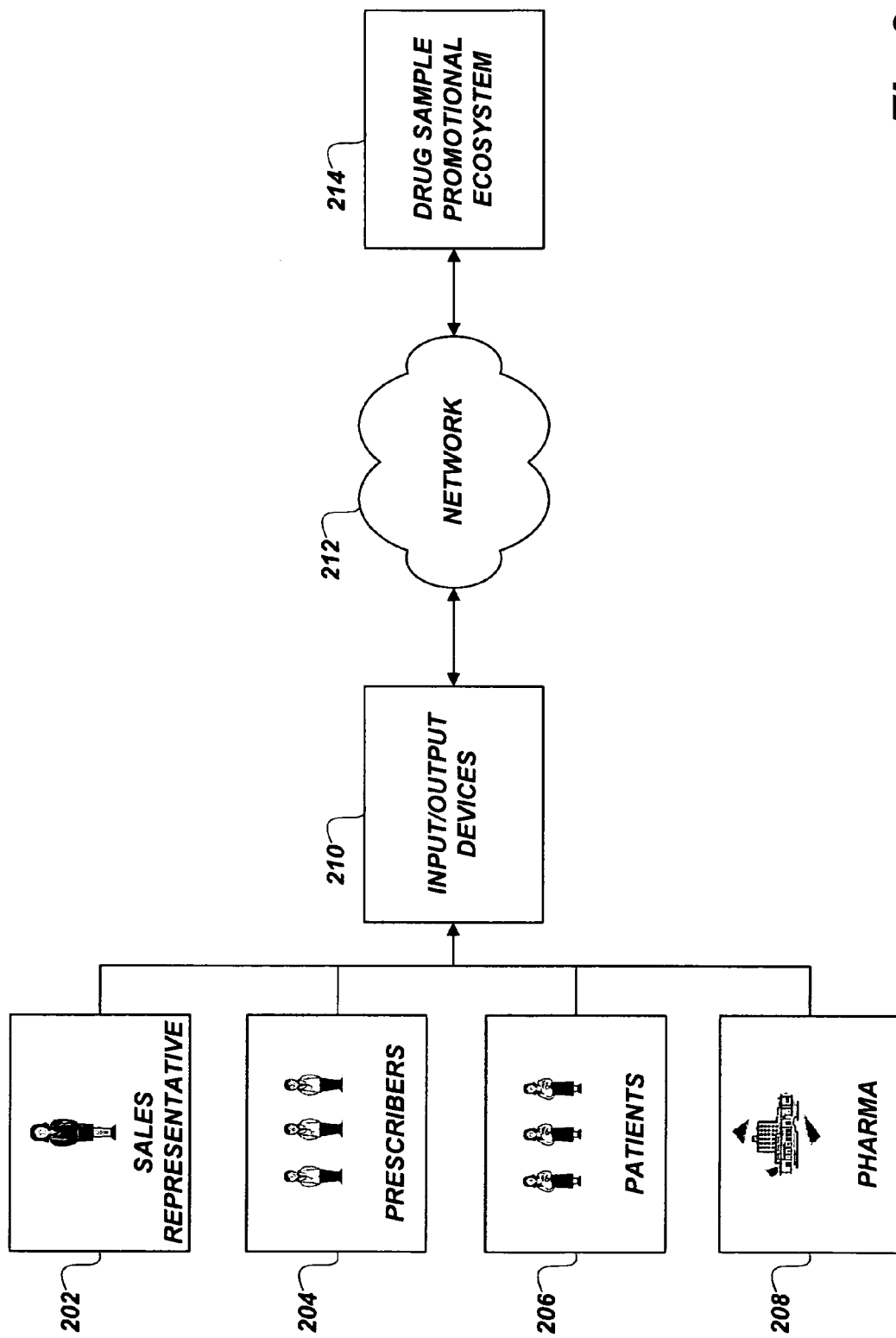
FIG. 2A is a block diagram illustrating pieces of a system for interacting with a drug sample promotional ecosystem, according to one embodiment of the present invention.
Figure 2B:
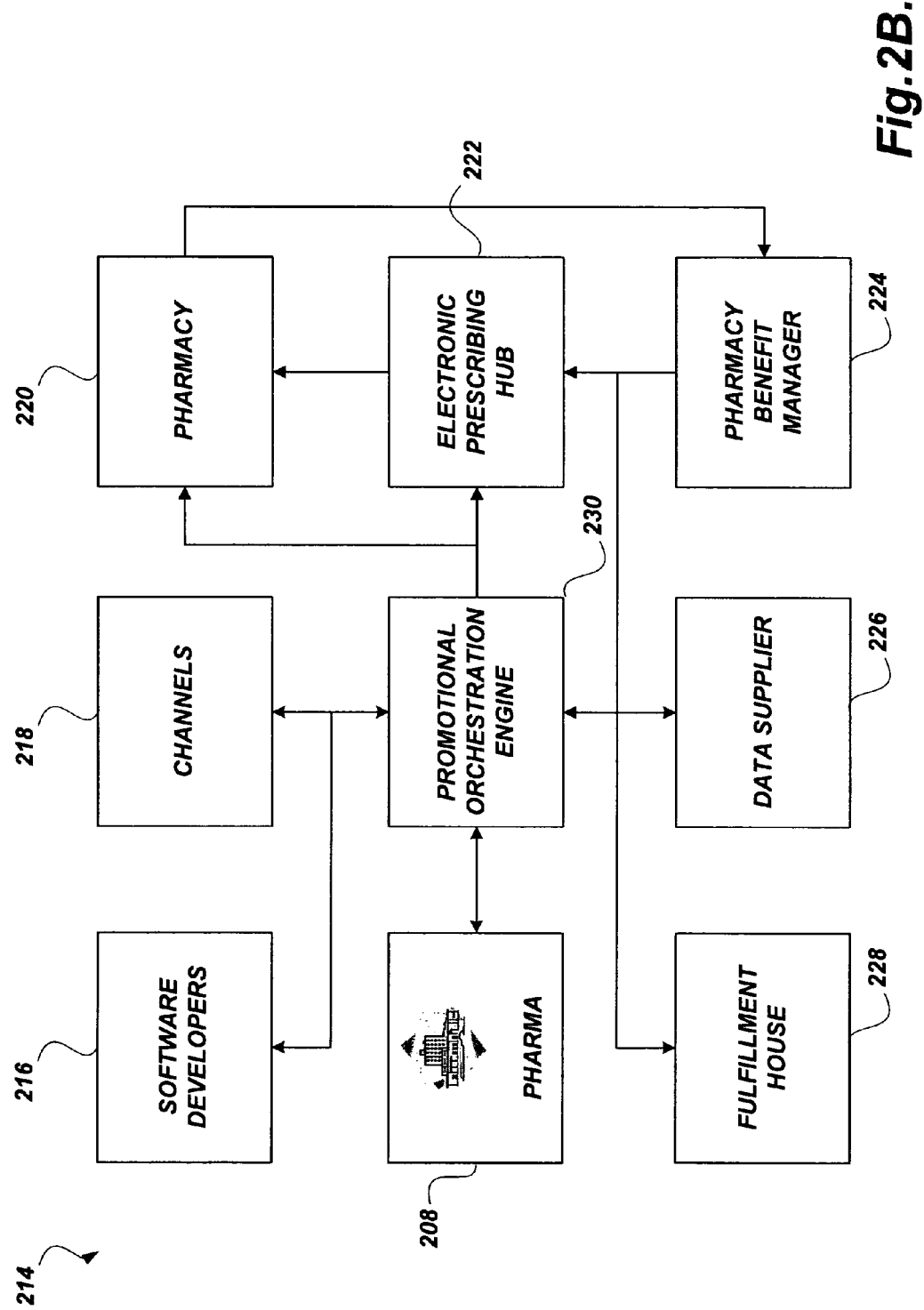
FIG. 2B is a block diagram illustrating pieces of the drug sample promotional ecosystem, according to one embodiment of the present invention.

FIG. 2A illustrates components of a system by which users are coupled to a drug sample promotional ecosystem 214. Sales representative 202 works for a pharma 208. The drug sample promotional ecosystem 214 is used by the sales representative 202 in conjunction with a Customer Relation Management software, Sales Force Automation software, or as an interface to a promotional orchestration engine 230 (FIG. 2B). The sales representative 202 preferably uses the drug sample promotional ecosystem 214 to identify high-value prescribers; respond to requests from prescribers for visits or physical samples; and other marketing or sales functions.

Prescribers 204 are authorized to provide drug samples. The prescribers 204 also use the drug sample promotional ecosystem 214 to request samples; sales representative visits; manage sample closet inventory; and obtain medical education information. Patients 206 are consumers who have been authorized by a prescriber, such as prescribers 204, to receive drug samples. The pharma 208 is a company engaged in the manufacture and sales of pharmaceuticals, which are medicinal drugs used for therapeutic applications. The pharma 208 accesses the drug sample promotional ecosystem 214 to obtain analytical data so as to obtain data generated by the drug sample promotional ecosystem 214 to formulate trends against information already available to the pharma 208. Marketing and sales departments of the pharma 208 can also obtain better return on investment analysis from the drug sample promotional ecosystem 214. This allows the pharma 208 to better focus and target drug sample distribution and sales efforts.

The sales representative 202, prescribers 204, patients 206, and pharma 208 access the drug sample promotional ecosystem 214 via a number of input/output devices 210. These input/output devices 210 include wired/wireless workstations, such as desktop computers, laptop computers, notebook computers, servers, and other similar hardware. Other input/output devices 210 include personal digital assistants; personal digital assistant proxies; telephones; printers, and facsimile communication machines. Input/output devices 210 are coupled to the drug sample promotional ecosystem 214 via a network 212.

The network 212 is a group of computers and associated devices that are connected by communication facilities. The network 212 can involve permanent connections, such as coaxial or other cables, or temporary connections made through telephone or other communication links. The network 212 can be as small as a LAN (local area network) consisting of a few computers, printers, and other devices, or it can consist of many small and large computers distributed over a vast geographical area (WAN or wide area network). One exemplary implementation of a WAN is the Internet, which is a worldwide connection of networks and gateways that uses the TCP/IP suite of protocols to communicate with one another.

FIG. 2B illustrates the drug sample promotional ecosystem 214 in greater detail. At the heart of the drug sample promotional ecosystem 214 is a promotional orchestration engine 230. Various partners are coupled to the promotional orchestration engine 230 to help facilitate distribution of drug samples, reports, and other services to users 202-208. Software developers 216 are those that develop software for Customer Relations Management systems, Sales Force Automation systems, and physician practice management systems. Although software developers 216 have no direct linkage to drug sample distribution, they are coupled to the promotional orchestration engine 230 so as to facilitate the interchange of specifications and plans to allow software products to produce interchangeable data with the promotional orchestration engine 230.

Channels 218 include pharmaceutical company Web sites, physician portals, consumer health portals, insurance companies, health care plans, and informatics companies that wrapped the functionality of the promotional orchestration engine 230 to provide such functionality through their own applications. The channels 218 are interfaced to the promotional orchestration engine 230 using any suitable means. One suitable means includes specific programmatic interface. Another suitable means includes an interface through a customizable, tag-based language, such as extensible markup language (XML).

The pharmacy 220 is one delivery vehicle for getting drugs to the patients. To do this, the pharmacy 220 typically needs a valid prescription or a valid sample voucher in either paper or electronic form. The pharmacy 220 dispenses the drug to the patient, then bills the patient directly (for those without health plans), bills the appropriate governmental agency (for those entitled to assistance) or to a pharmacy benefit manager 224 (for those on health plans).

An electronic prescribing hub 222 is a commercial venture, which supports electronic prescribing. To use an electronic prescribing hub 222, the prescriber transmits a prescription to the pharmacy 220 via the electronic prescribing hub 222. The pharmacy benefit manager 224 uses the patient information from the electronic prescription, checks to see whether the prescription is partially or fully covered, and communicates with the prescriber to obtain an alternate prescription because of non-covered or partially covered drug results. A fully covered drug or a partially covered drug that is authorized by the prescriber generates an electronic prescription to the pharmacy 220 where the patient will pick up the drug or drug sample. The promotional orchestration engine 230 may transmit an electronic voucher directly to the pharmacy 220 without having to go through the electronic prescribing hub 222. Alternatively, the promotional orchestration engine 230 may transmit the electronic prescription directly to the electronic prescribing hub 222, as if the promotional orchestration engine 230 were a subscribing health plan.

The pharmacy benefit manager 224 is an entity, which, for a fee, mediates prices for drugs with the pharma 208, the pharmacy 220 and health care plans. When a prescription is issued, the issuing pharmacy 220 bills an appropriate pharmacy benefit manager 224. The pharmacy benefit manager 224 pays the pharmacy 220, and bills the patient's health plan for the price agreed upon by the plan and the pharmacy benefit manager 224. The pharmacy benefit manager's 224 profit comes from claims processing fees. Health plans use pharmacy benefit manager 224 because it is cheaper than negotiating contracts themselves without the overhead.

A data supplier 226 provides information such as demographics, prescriptions, prescribers, economic trends, and prescribers' identification and licensing information. The promotional orchestration engine 230 uses sample distribution and usage as proxy and leading indicator for prescriptions. Using external information provided by the data supplier 226 allows the promotional orchestration engine 230 to adapt it to external trends. For example, a drop in drug sample order volume may be due to the nature of the economy and not because of the undesirability of the drug sample. The data supplier 226 may supply economic data so as to allow the promotional orchestration engine 230 to take that information into account and not change the system inappropriately.

A fulfillment house 228 is a company that supplies sales representatives and prescribers with drug samples and promotional materials. When dealing with drug samples or other controlled materials, the fulfillment house 228 typically verifies the identity of the requestor by using a signature. The promotional orchestration engine 230 helps to facilitate the business processes of the fulfillment house 228 because the promotional orchestration engine 230 may alert the fulfillment house 228 electronically of a request for drug samples. The fulfillment house 228 may also use the promotional orchestration engine 230 to introduce a new medical or pharmaceutical product that lacks the attention of sales representatives. The pharma 208 is also a partner to the promotional orchestration engine 230. The pharma 208 provides rules for authorizing sample distribution and tracking these drug samples.

When a user 202-208 initiates a request to the promotional orchestration engine 230, the user 202-208 has access to the services made available by the promotional orchestration engine 230 unless certain restrictions have been placed on the user 202-208 by law, the pharma 208, the channels 218, and other partners of the promotional orchestration engine 230. For example, a prescriber-oriented online portal may require that drugs from a certain pharma appear first in an online presentation to a user 202-208. Many suitable actions may be invoked by the user 202-208 from the promotional orchestration engine 230. The user 202-208 may use the promotional orchestration engine 230 to check available drug sample status or examine educational materials. If the user 202-208 is a prescriber, the prescriber may print a sample voucher to distribute the sample voucher. If the user 202-208 is a prescriber and is using an automated inventory system compatible with the promotional orchestration engine 230, the promotional orchestration engine 230 obtains current inventory status and issues automated reorders to pharma or fulfillment houses 228 for products where such reorders are allowed. For products where automated reorders are not allowed, the user is provided a reminder that a reorder is needed.

Another activity that can be performed by the user 202-208 through the promotional orchestration engine 230 is issuing an electronic prescription for a drug sample in the form of free medication to be dispensed by a pharmacy if the user 202-208 is a prescriber. This may be for cases where samples for certain drugs are not available, or when keeping drug samples in a sample closet creates problems (such as managing controlled substances or when specialized storage is required). Electronic sample prescriptions may go through an intermediary, such as the electronic prescribing hub 222 or directly to the pharmacy 220. If the user is authorized to order supplies from a fulfillment house 228, the user 202-208 may interact with the promotional orchestration 230 to generate an order to be sent to an appropriate supplier. This may involve printing a request so that the user 202-208 may sign and fax the request or it may involve direct transmission of the request with an electronic authorization and authentication. The promotional orchestration engine 230 also allows the user 202-208 to request information about a particular drug, promotional items from a pharmaceutical company, request for a sales representative visit, view online drug information, or obtain an electronic detail (an online drug-specific or disease specific education program). Furthermore, the promotional orchestration engine 230 allows information to be sent from or to the promotional orchestration engine 230. This includes data exchanged with other systems, such as customer relation management. The promotional orchestration engine 230 allows generation of data files for secure transport or interchange of data with other electronic systems via a common language, such as XML.

Figure 2C:
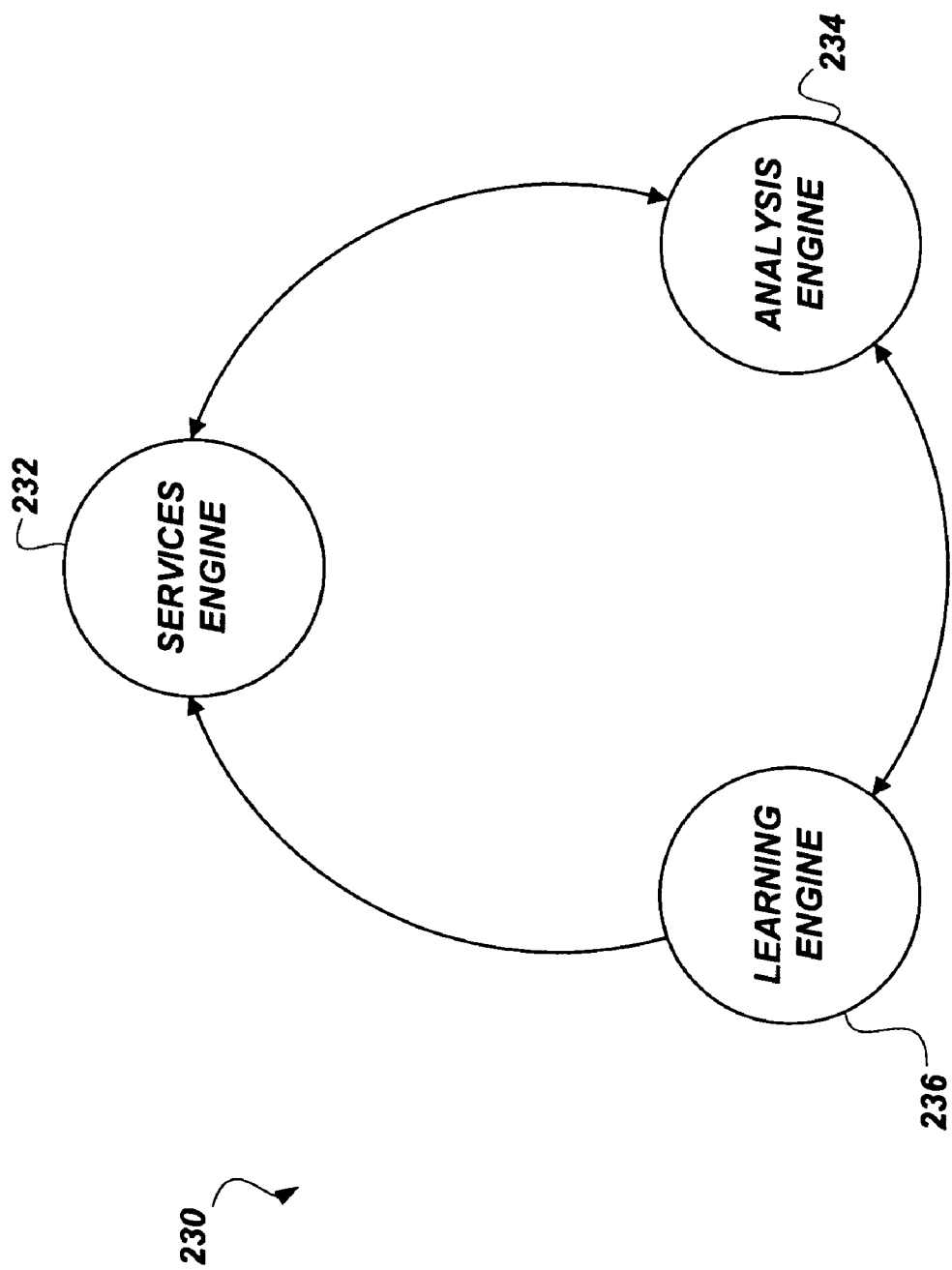
FIG. 2C is a block diagram illustrating pieces of a promotional orchestration engine, according to one embodiment of the present invention.

The promotional orchestration engine 230 is illustrated in greater detail at FIG. 2C. A services engine 232 provides user interface functionality, such as sample request generation, inventory management, and sales representative services. The services engine 232 is transactional in that a user's request to the services engine 232 typically results in information being returned to the user or request for further actions that will be forwarded to the channels 218, the pharma 208, and suppliers (fulfillment house) 228. An analysis engine 234 stores data and provides tactical and strategic level analysis. The analysis engine 234 uses transactional data generated by the services engine 232 to extract knowledge and consolidate and aggregate such information. For example, the analysis engine 234 consolidates information from preferences of a prescriber with demographic information, usage data, and prescription data. Such consolidation generates a profile of the prescriber that allows the promotional orchestration engine 230 to predict what sort of products a prescriber is likely to need or be interested in next.

The learning engine 236 is a mechanism by which the promotional orchestration engine 230 adapts itself to changing conditions. The learning engine 236 preferably customizes various components of the services engine 232 and components of the analysis engine 234. The learning engine 236 uses information from the analysis engine 234 and from the pharma 208, the fulfillment house 228, and channels 218 to determine the proper configuration and information for presenting to a user 202-208. The learning engine 236 causes the services engine 232 to present different information over time so as to keep the system fresh. From a user's standpoint, the learning engine 236 allows components of the services engine 232 to be personalized to the particular user.

FIG. 2D illustrates the services engine 232 in greater detail. The services engine 232 provides basic transactional functionality of the promotional orchestration engine 230. The user interface 262 is the portion of the application suitable for human interaction. It includes Web pages customized to meet capture/display device requirements (e.g., there may be different pages for conventional workstation Web browsers and for PDA Web browsers); an automated voice response (AVR) system for those using an automated interface via telephones; and human assistance, e.g., a call center. An API interface 264 is the portion used for interchanging data and information with other applications; as such, it is the gateway to core functionality for channel partner applications, which wrap core functionality. The API may be generic (suitable for multiple channels) or specifically tailored to a given channel. The API may also use either encrypted or unencrypted transport depending on the security needs of the specific interface.

Inventory management 238 is a service that allows a prescriber office staff to manage the contents of the prescriber's sample closet for physical, electronic vouchers, paper coupon samples, and other suitable forms of samples. This includes: automated reorder of vouchers and coupons if the existing stock is depleted, whether allocation limits have been reached, or the stock has reached expiration dates; reminders for physical sample reorder when stocks are expected to be low; usage reporting; inventory status; and some limited patient compliance checks. Replenishment and tracking of samples requires the prescriber to use a compatible inventory system. This will generally be an automated system (although limited manual functions will also be provided) and generally in the form of a PDA or workstation which maintains a list of the prescriber's sampling activities and synchronizes at intervals with the promotional orchestration engine 230. The interface to the client device may be manual or automated.

Inventory management 238 covers several functions for an individual prescriber virtual sample closet: maintain a count including history of previous orders of the number of paper vouchers and physical samples requested; allow a prescriber to update the quantity of physical samples and paper coupons in the prescriber's sample closet; automatically decrease the count of paper samples when a paper sample is ordered; automatically prepare and/or issue a replenishment order when the sample quantities in the sample closet fall below a reorder point; automatically issue a replenishment reminder when the expiration dates of previously printed vouchers have been reached or if the remaining quantity (the number originally printed less the number redeemed) falls below a reorder point; automatically issue a reminder to reorder when the quantities of physical samples in the sample closet fall below a reorder point; for patient compliance with e-vouchers, issue a "tickler" to the prescriber indicating whether the voucher has been redeemed (i.e., the patient picked up the sample); and for patient compliance with e-vouchers, if a sample was redeemed issue a "tickler" to the prescriber when the sample has run out (i.e., the patient should have used all the sample).

Representative visit scheduling 244 is a service that allows the user (assuming the user is authorized to do so) to request a visit from a pharma sales representative. These representative visits are highly prized by sales organizations because they represent "face time" with the prescriber. A request for a visit is extremely valuable because many drop-by visits by representatives result in little contact with the prescriber.

Sales representatives can also use this service to adjust their call schedules and activities based on prescriber preferences: for example, a prescriber may change preferences for see/no-see, sample/no-sample, delivery or form preferences, or therapeutic class interest. This allows the sales representative to adjust call patterns, the services the sales representative will offer on a visit, the material the representative will leave with the prescriber and so on. If the representative is using Customer Relation Management (CRM) or Sales Force Automation (SFA) software compatible with the sales representative visiting schedule function, the information used in this function can be automatically loaded to the CRM/SFA software and automatically integrated with the other tasks the sales representative is to perform. Representative visit scheduling 244 captures several pieces of information: prescriber name; prescriber address; prescriber telephone/fax/e-mail; drug(s) for which visit is requested; date and time at which the visit is requested; special request (e.g., bring samples, bring literature, multiple prescribers will be present, etc.). The sales representative visit scheduling supports: links to compatible SFA/CRM systems for automatic updating of rep task lists; consolidation of requests (a sales representative gets a single list of requests from all prescribers based on which drug the sales representative covers; the sales representative does not have to search for information by individual prescriber); priority-setting in that the receiving sales representative can designate specific prescribers as higher importance or designate groups of prescribers to have higher priority based on criteria such as geographic proximity of the prescribers (e.g., clusters get higher priority than individuals), specialty, sampling deciles, and so on.

Physical samples, vouchers and e-coupons 250 is a service that authorizes users to create sample prescriptions without using an Electronic Prescribing Hub or an electronic signature system. Physical samples are requests to suppliers—usually fulfillment houses—for a physical drug sample. The process of obtaining phsyical samples starts with a paper or electronic request generated within the promotional orchestration engine and sent to the supplier: the user requests physical samples from the promotional orchestration engine; the promotional orchestration engine validates that the user is authorized to receive this drug sample; the promotional orchestration engine issues an electronic "early warning" to the supplier that a request for physical samples is imminent (details are included in the notification); the promotional orchestration engine displays a phsyical sample request page suitable for printing and signature; and the prescriber faxes the signed page to the supplier before the supplier will issue the samples. An electronic authorization and authentications, such as digital signatures, provides a means of eliminating the manual steps for obtaining drug samples. The presence of a valid electronic authorization and authentication will allow the promotional orchestration engine to confirm to the supplier the request is valid and eliminate the need for a faxed signature. The promotional orchestration engine also has the ability to allow the supplier to update the status of the request, e.g., awaiting prescriber signature, awaiting shipment, shipped, delivered and signed for.

Samples include prescriptions, locally printed on-demand or in a batch, which the prescriber signs to validate. The process for obtaining various samples can be different. Samples, such as a voucher, may also be sent through an Electronic Prescribing Hub or to a pharmacy; in this case, the samples are signed digitally by the prescriber and transmitted electronically to the electronic prescribing hub or pharmacy instead of being printed. Whereas voucher samples are used by prescribers, electronic coupon samples may be oriented to prescribers or direct-to-consumer. For voucher samples, the process to obtain includes: the prescriber selects the desired drug sample (including dosage and format) from the list of samples the prescriber is authorized to receive (the authorization rules come from the supplier); the prescriber is presented with appropriate documentation on the use and limitations of the voucher and must accept this before proceeding; the prescriber is asked how many voucher samples the prescriber intends to print; the voucher sample may be displayed, customized to the degree possible for the prescriber; the prescriber prints the voucher sample on his/her local printer; the prescriber signs the voucher sample and presents it to the patient; the patient takes the signed voucher sample to a pharmacy where it is treated exactly like a prescription; billing for the dispensed drug is made to a party operating the promotion orchestration engine and by such a party in turn bills the authorizing pharma or channel.

Electronic coupon samples include OEM coupons from pharmas or other coupon processors like McKesson and those hosted by the promotional orchestration engine. These electronic coupon samples typically specify the dosage and format. The patient or prescriber usually prints a copy which the prescriber then signs. The signed coupon sample commonly then entitles the patient to a free physical sample from a pharmacy, money off on a prescription, or extra quantities when redeemed in conjunction with a prescription. Additional promotions offers, such as mail-in rebates, cents-off coupons, and so on, can also be printed by prescribers, provided to patients, who then follow the promotional offer instructions to obtain price discounts via alternative systems, such as via mail to fulfillment houses, through coupon redemption systems, or the banking systems.

Prescribers with automated prescription systems (e.g., systems on handheld computers) can use those systems to issue vouchers. The process for using automated prescription systems is as follows: The prescriber selects the desired drug sample (including dosage and format) from the list of samples the prescriber is authorized to receive (the authorization rules come from the supplier); the prescriber is presented with appropriate documentation on the use and limitations of the voucher; the prescriber electronically or digitally signs the limitation document and is present with the voucher; the prescriber electronically or digitally signs the voucher; and the promotional orchestration engine electronically transmits the voucher to an Electronic Prescribing Hub or directly to a pharmacy depending on requirements and rules.

Voucher samples and electronic coupon samples may be accessed in several ways. At a minimum, users access coupons and e-vouchers by: pharma; therapeutic class; health plan; search preference list. This allows the user to select drug samples based on brand, use, or on whether the patient's health plan authorizes a particular drug. This promotes utilization of a specific health plan formulary for treating patients enrolled in that plan.

One aspect of the service 250 is the ability of the pharma or channel to set automated rules on distribution. For example, a user may or may not be allowed to request based upon: prescriber behavior; how many samples have been requested by the prescriber in a given time; whether the prescriber has had mandatory education (e.g., an e-detail); whether the prescriber will accept a rep visit; prescriber trend data; allocation limits for that specific prescriber or a group to which the prescriber belongs; whether the user has completed a specified number of e-learning sessions.

The e-learning link service 256 is an educational services offering. E-learning provides electronic remote education to prescribers about specific drugs. The process works by sending a prescriber from the e-learning site to a promotional orchestration engine but the process works equally as efficiently if the prescriber can be sent to the e-learning site from within the promotional orchestration engine. For example, a prescriber requesting a new drug might be sent to the e-learning site for that drug if the promotional orchestration engine records show the prescriber has not completed necessary training. E-learning is accomplished by either automatically routing a user to an e-learning site or by "wrapping" the e-learning site within the services engine 232.

Patient assistance service 240 is a program available from the pharmas for indigent or low-income care. Since drug samples are frequently used by prescribers to provide these patients with free medication, the ability to calculate accurate return on investment for drug sampling is compromised, and the patients may not receive the full range of medications available to them. To generate a more accurate return on investment for sampling, the use of drug samples for humanitarian reasons need be better understood. The patient assistance service 240 makes it easy for prescribers to register appropriate patients for official patient assistance programs. A patient that is in the assistance program is a patient that can receive samples through a controlled patient assistance program, and the use of drug sample for non-trial purposes is therefore minimized.

The patient assistance service 240 has a process to identify, control, and provide drug samples used for indigent or low-income patients: the prescriber enters the therapeutic class for the desired drug; the promotional orchestration engine determines if any assistance programs offer this class and, if so, which ones; if there are drugs available in the class, the promotional orchestration engine presents a simple Web page allowing documentation for the request (most eligibility requests involve the same information, just structured differently); with the data from the Web page, the promotional orchestration engine evaluates eligibility using the criteria for each assistance program; the promotional orchestration engine presents a list of candidate drugs or a set of reasons why eligibility was not met; the prescriber chooses the drug for the patient; and the promotional orchestration engine either prints the appropriate documentation so it can be sent to the pharma or transmits it electronically if the pharma is equipped to handle electronic requests. Applications for drug discount card programs can also be made available to the prescriber to provide to eligible patients via the promotional orchestration engine as part of the patient assistance module.

Pre-enroll services 246 are used when a pharma or channel wishes to enroll a large number of validated users at one time. This reduces system load, improves user performance, and allows the pharma or channel to specify exactly which prescribers have access to which services. Pre-enroll services 246 require the pharma or channel to supply an electronic file with the information in a standard format; standard database loading and transformation queries are then used to move the information from the supplied database to the promotional orchestration engine database.

Pre-enrollment may also be implemented by either preloading only recruited users or by preloading and activation. In the former approach, the promotional orchestration engine is configured with a list of specific users, all of whom will be given access to the system. For example, a given specialty may be given access to services, so the data provided will be a complete list of those in that specialty: they are all simultaneously activated.

The preloading and activation approach is more sophisticated. In this mechanism, users are pre-populated into the promotional orchestration engine database but are left in an inactive status. The status is switched to active and the promotional orchestration engine becomes available to the user based on recruiting or other activities; for example, a marketing campaign might start with prescribers in a given locale, then roll out the program to other locales by activating the users in those areas in a specified sequence. Since there is full control over what the user is able to do in the promotional orchestration engine, this also applies to services. A pre-enrolled user can immediately have access to a full set of services or have those services rolled out in a coordinated campaign. This combination of being able to activate users on anything down to an individual basis coupled with service activation control lets recruiting efforts be tightly targeted.

Representative services 252 are present to assist sales representatives with planning and implementing sales visits. Representative time is valuable and the representatives want to concentrate their time on prescribers who write the most prescriptions. Representative services make use of the analysis engine to: identify the best candidates for office visits (i.e., prescribers who sample a lot based on the trendline analysis) identify future high prescribers (prescribers whose rate of sample use is increasing based on trendline analysis and matrix matching); identify which message to "push" to a prescriber based on prescriber behavior based on matrix matching: by comparing which messages worked well for similar groups/profiles, a rep can establish an appropriate approach for marketing to prescribers. For example, when two otherwise similar groups of prescribers receive different messages and one prescriber uses a noticeably greater number of samples compared to the other, it is likely that the message made a difference. This lets representatives tailor messages to clientele.

Representative services 252 also support basic "blocking and tackling" marketing functions such as SFA software integration (the promotional orchestration engine) which provides integrated linkage for appointments, task lists, and similar functions; examination of customer history, which prior to a visit to a prescriber, the representative can view some elements of the prescriber behavior such as recent sampling and new prescription data. This lets the representative customize the presentation to the prescriber to more closely match what the prescriber is doing; printing or ordering coupons, e-vouchers, and other materials that provide enough value (e.g., customized coupons) that a prescriber will take the time to see the rep; personalization of paper samples and coupons to specific prescribers and specific representatives; printing to local copy services (such as Kinko's) for high-volume requests instead of using a local printer, which includes use of standardized templates (e.g., producing coupons for the same product in a variety of page layouts and being able to order specialized services such as binding or trimming through the promotional orchestration engine); allowing the representative to order new sales collateral from pharma or other suppliers; participate in "ask/answer" bulletin board conferencing with other representatives, which can be open (accessible to reps from various pharma or sales organizations) or restricted (limited to a specific set of reps as determined by the discussion owner); receiving new training or educational material from the representative's employer (source materials may be placed into the promotional orchestration engine by the pharma or sales organization and accessed by the rep: this is the same technology as applies to the knowledge base but is specifically using source materials targeted to representatives; updating to show whether a visit was successfully arranged and completed. Representative services are implemented by specific subservices (e.g., the bulletin board) and a service-based interface to the data warehouse supported by the analysis engine 234. Pre-programmed scripts (specifications defined by the rep employer) are available as well as limited ad-hoc queries through the warehouse itself.

Pharma services 258 are services oriented towards reporting the results of sales and marketing initiatives. Pharma is very interested in identifying prescriber behavior and groups that are more likely to have higher prescription rates. These functions are intended to let pharma analyze trends and behaviors to more effectively sharpen their marketing. Like representative services 252, pharma services 258 make extensive use of the analysis engine 234. The pharma service 258 allows access to the underlying analysis engine 234 data in real time or near real time. In addition to pre-built reports such as samples used by drug, representative, area, therapeutic class; trends by drug, representative, area, therapeutic class; new prescriptions by drug, representative, area, therapeutic class; and lagged and current period comparison of samples vs. prescriptions by drug, representative, area, therapeutic class.

Pharma services 258 use much of the same data as representative services 252 in the analysis engine 234 but also make extensive use of data from external sources. Data from external sources, particularly specific prescriber prescription data, is necessary to demonstrate the link between samples, new prescriptions and total prescriptions and document the mathematics of that linkage. The other major pharma use of the promotional orchestration engine, setting up rules and allocations, is contained in the learning engine 236.

The knowledge base 242 is a collection of useful services (Ask/Answer, Medical Education, journal article reprints, and so on) that let prescribers and other users search for information in a single place. The service 242 includes Web pages containing links to documents stored in promotional orchestration engine coupled with a simple Web search engine. The service 242 also includes a Web-based interface to a commercial document management system and knowledge engine which allows plain English queries. The knowledge base 242 reflects some activities of the promotional orchestration engine itself, for example, list the 10 most frequently accessed articles; list the 10 most frequently accessed articles for prescriber's specialty; list the 10 most frequently accessed articles for prescriber's zip code; list articles related to this one; list articles by therapeutic class; list articles by drug; list articles by pharma. To do this, the promotional orchestration engine not only store articles but for each article stored it tracks accesses by prescriber specialty; accesses by zip code; using "nautilus" code that correlates article relationships and therapeutic classes; and authorship.

Personalization/customization 248 is a service that allows the user to customize the promotional orchestration engine experience to some degree. For example, a user may be able to specify which drugs appear in the user's home Web page and the order in which those samples appear. Personalization/customization also allows the promotional orchestration engine to adapt itself to the user's behavior over time. The learning engine 236 portion of the promotional orchestration engine combines with the analysis engine 234 to analyze the behavior patterns of a given user, the learning engine can customize the personalization/customization setting so that even if the user never customizes the service engine interface, the interface will still gradually adapt itself to the work the user performs.

Personalization/customization involves access to the data elements detailed in the prescriber preferences and usage components of the analysis engine 234 plus tracking some additional items, among which are use of the knowledge base and Patient Assistance (e.g., which articles are accessed, which assistance programs are used); the contents and order of the drugs in the prescriber's personal virtual sample closet; e-learning; representative visits requested/completed.

Personalization/customization processing is at the base largely a matter of counting. The things done most frequently such as access to specific drug samples, requests for visits, looking up specific information in the knowledge base 242 are likely the things the prescriber values most. The promotional orchestration engine 230 moves these to a personalized "home page" for that prescriber. This page may be different than that for any other prescriber because its contents and the order of the contents are based on what that specific prescriber has done in the past and the preferences he or she has established.

Patient education 254 is the service that allows patients and potential patients access to education, starter kits, and similar patient-oriented materials for patients who have begun or may be about to begin a drug regimen. Pharmas often produce patient education material that explain the specific condition they may have, describe proper use, dosage, side effects, interactions, and storage of drugs which are intended to help patients use the drugs properly and with minimal risk. These materials may or may not be provided with a drug sample; this implies that drug samples given to a patient who does not receive education material may be riskier than those given to a patient who did receive them since the patient lacks vital information. Patient education material may be provided to the patient by the prescriber (the prescriber prints them locally or orders them via the promotional engine), the prescriber provides the link to the promotional orchestration engine 230 to that the patient can obtain his/her own material, or the patient may search out the information on his/her own.

Recruiting services 260 are pharma-oriented services which allow pharma marketing users to initiate recruiting campaigns. These services work in conjunction with the recruiting profiling functions of the learning engine. In brief, these cooperate to provide both recommendations for prescriber selection and the means to use those recommendations immediately. The recruiting profiling function of the learning engine 236 provides demographic and performance based profiling based upon the success or failure of earlier recruiting. This allows the user to quickly refine which characteristics are most important to recruiting candidates who will make use of samples of that particular drug. The recruiting services function of the services engine 232 takes the prescriber set(s) created by the recruiting profiling function and allows the user to initiate contact campaigns directly. This includes features such as generating accounts (using the pre-enroll service), creating digital keys, mass e-mailings, special online promotions within partner site communication, and so on.

In a typical scenario, a pharma user would begin with a need for 500 prescribers to be recruited for a product launch. Using the recruiting profiling functions in the learning engine 236, the user determines that the best launch strategy is to target prescribers who use a certain drug therapeutic class and not on geography or specialization. The recruiting profiling function indicates there are 400 such prescribers available via recruiting services 260. The user then instructs the recruiting profiling function to transfer those prescribers to the recruiting services function. The prescriber information is not completely displayed to the user: the user sees a blinded set of information that does not allow identification of specific prescribers. This is for both prescriber privacy and to prevent use of this information outside the system in ways which may be incompatible with usage policies. The blinded set is presented to allow the user to select or deselect specific individuals based on displayed information. The user then invokes the recruiting services functions. These functions allow the user to select common recruiting approaches—for example, using e-mail—and the content of those approaches (e.g., upload a PDF brochure to accompany the e-mail) from a set of standardized recruiting tools. Additionally, the user can request specialized services. When the request is completed, it is forwarded by the system to a coordinator for pricing if pricing has not previously been established. Once suitable pricing has been agreed to by the client, the recruiting request is authorized by the coordinator and execution begins. Certain functions such as mass e-mailing potential recruits using the collateral provided by the pharma user can take place immediately for the prescribers known to the system. Functions like recruiting through partner portals may benefit from manual processing.

At the time the recruiting request is executed, an entry is made into the recruiting profiling data indicating the criteria for selecting the recruits, the prescribers selected, and the drug for which the recruiting is being done. As requests for samples are processed, this information is used to augment the recruiting profiling data to indicate response rates and times. This provides the basis for the recruiting profiling function of the learning engine 236 to evaluate how well the recruit group responds to the campaign. This allows those functions to make better recommendations for future campaigns.

Figure 2E:
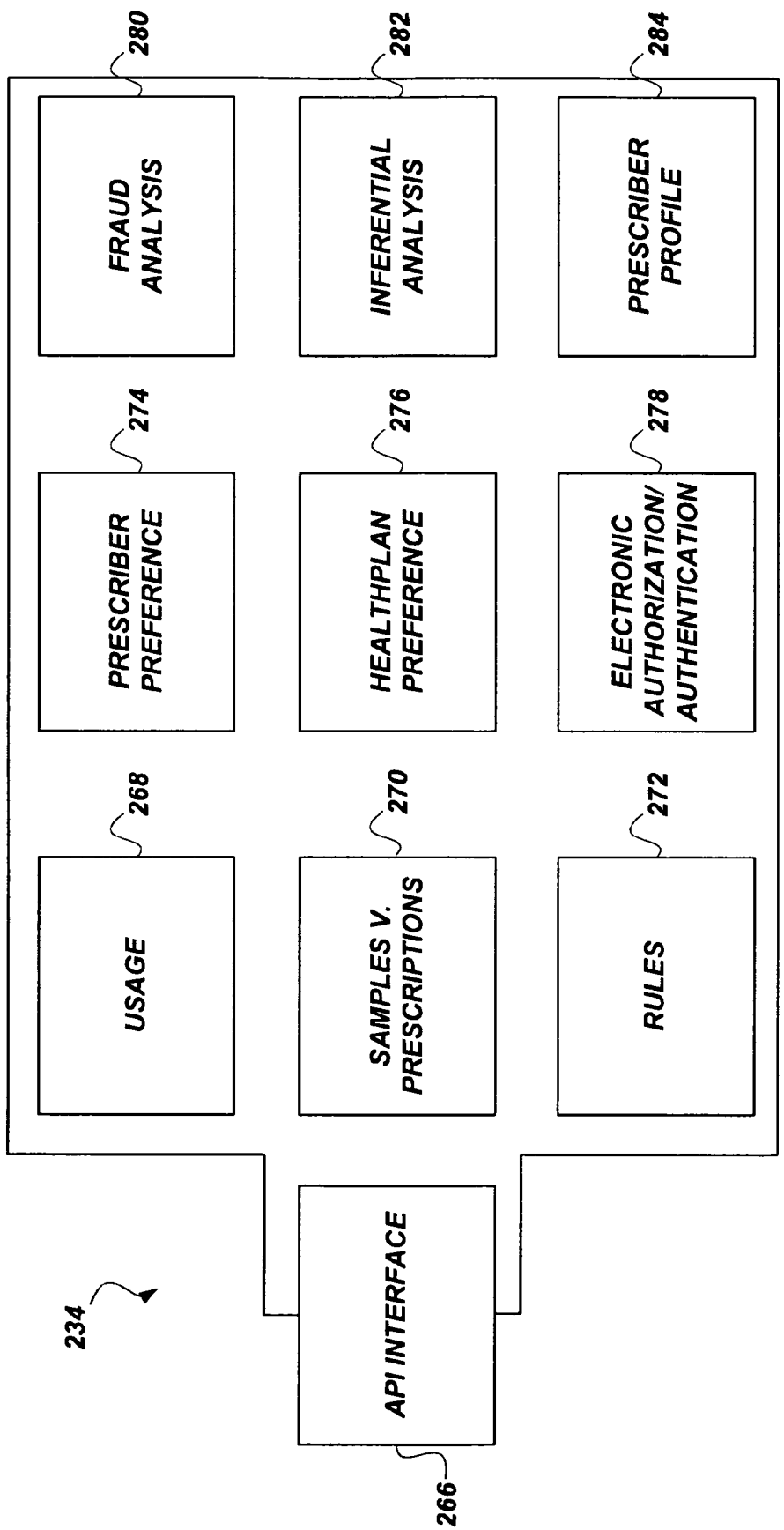
FIG. 2E is a block diagram illustrating pieces of an analysis engine, according to one embodiment of the present invention.

The analysis engine 234 captures actions taken by a user of the system for recordation and analysis. See FIG. 2E. These actions of the analysis engine 234 help to allow the learning engine 236 to better adapt the services engine 232 to the user; facilitate return-on-investment calculation on sampling by tracking sampling versus prescription activity by prescriber and prescriber group; to allow analysis and segmentation of users based on how the users interact with the services engine 232 (e.g., we might find that cardiologists use the knowledge base 242 more than other general practitioners, so marketing to cardiologists might thus tilt to informational approaches instead of representative visits); to provide customers of the promotional orchestration engine 230 with useful information about the effectiveness of marketing (e.g., we might find that use of the system is tied directly to marketing done in certain magazines targeted towards specific prescriber segments and is negatively correlated to consumer coupons in newspapers); to provide tracking for coupons and e-vouchers; to allow "profiling" for inferential analysis. Since the user population for the system is more or less statistically distributed, it should be possible to draw a profile of a hypothetical "average" user of the system by demographic and specialty. Combining the "average" user with the specific preferences of the user expressed in the services engine 230 allows a highly targeted campaign with a lessened risk of narrowing the focus of the individual user too much—the individual preferences will be constantly trying to narrow the focus, the "average" user preferences to widen it. The technologies underlying the analysis engine 234 include both transactional databases and data warehouses; the former are used primarily to store information, the latter to consolidate and analyze it.

The API component 266 is the means by which information is sent into or extracted from the analysis engine 234 by external sites. Using a specific API allows these sites to build applications which work reliably using analysis engine 234 data and at the same time provide a degree of protection to the analysis engine 234 by making it unnecessary to expose the inner workings of the analysis engine 234 proper. APIs will at a minimum be provided for: remote channel login; launch customized interface; voucher and e-coupon generation, serialized or otherwise; graphics rebranding (allow a pharma company or a channel partner to add in its own graphics); all external data suppliers (necessary because information is being provided in proprietary formats).

The usage component 268 of the analysis engine 234 tracks prescriber sampling activities, among them: which user is accessing the promotional orchestration engine; when and how frequently the user accesses the promotional orchestration engine; what services are invoked (e.g., e-vouchers, rep services, literature request, physical sample requests, e-learnings, etc.); what requests were made from each service (e.g., how many e-vouchers were printed); and how many sample coupons/e-vouchers were requested, printed, redeemed. In other words, the usage component 268 of the analysis engine 234 tracks how a specific individual user actually works with the promotional orchestration engine 230.

Samples vs. prescription component 270 is targeted to provide correlation between drug samples, new prescriptions, and total prescriptions. The sample vs. prescription component 270 tracks samples using the inventory management service, representative services, e-voucher, coupon, and physical sample services, and compares the sampling activity against statistical profiles of prescriptions by drug and area to generate a model of sampling versus prescribing activity.

The analysis engine 234 compares lagged sample usage (contained in the usage component 268) against prescription data obtained from outside vendors. The usage component 268 tracks not only how the promotional orchestration engine is being used but what it does. For example, it determines which physical drug samples are requested, which vouchers and coupons are printed and redeemed, which paper coupons are requested and used. By comparing the total number of samples issued at periods in the past (for example, 120, 90, 60, and 30 days) against prescriptions, the analysis engine 234 establishes a correlation: for example, an increase of 20% in sample use 120 days ago may correlate to 5% increase in new prescriptions in the current period. A justifiable inference is that the two are cause and effect: 25% of those issued samples will shift to prescriptions approximately 4 months later. The promotional orchestration engine 230 can provide this sort of knowledge to better strategize a drug sampling promotional campaign.

The rules component 272 of the analysis engine 234 is provided with a specific service request and user ID and uses information from the learning engine 236 and the analysis engine 234 to determine if the request should be serviced. For example, if a prescriber wishes to print e-vouchers for a particular drug, the rules component 272 can return one of four responses based on the drug and that particular user: OK; OK with an allocation limit; OK after conditions are met (e.g., the user must complete an e-learning before being allowed to print); and refused for various reasons.

The rules component 272 provides a convenient means for the services engine 234 to ensure compliance with pharma, partners, and fulfillment house rules without embedding the coding for those rules in the services engine 234 proper. This makes the system more flexible and changes to rule structures and data easier to manage with less impact to the remainder of the promotional orchestration engine 230. Rules may be either static or dynamic. A static rule is one that does not change based on prescriber or user behavior. For example, there might be a rule that only 10 live samples of a particular drug may be requested in a given 90-day period. A dynamic rule is one that may result on different actions based on prescriber or user actions. For example, a dynamic rule may say "only 10 physical samples may be distributed in any 90-day period unless the requester agrees to a rep visit; the rep visit automatically authorizes an additional 10 samples." The rules component 272 is able to evaluate a request based on any combination of: whether/how many e-learnings have been done by the user for that drug or pharma; whether/how many rep visits have been done by the user for that drug or pharma; how many samples have been requested within a specified period; how many samples have been printed within a specified period; how many samples have been redeemed within a specified period; the prescribing decile for the user (if applicable) by location, specialty, therapeutic class; user specialty (if applicable); and sample to prescription conversion rate for the prescriber within a specified period. The data for the tests can be found in the usage component 268 and samples vs. prescription components 270 of the analysis engine 234.

Prescriber preferences component 274 track how the user says they would like to work with the promotional orchestration engine. These are preferences which are generally visible to and modifiable by the prescriber such as see/no see; sample/no sample; delivery preference (mail, rep, online); form preference (physical, coupon, e-voucher); sampling interest (e.g., individual prescriber sample closet); and survey and information mailing opt-ins. This information is used in conjunction with activity information by the analysis engine 234 and learning engine 236 to continuously adapt and modify the way the promotional orchestration engine interacts with the prescriber.

The health plan preferences component 276 records the drug preferences of various health plans. This is important for drug sampling since not all plans cover all drugs and the prescriber will likely wish to provide the patient with samples of drugs that are covered under the patient's health plan. The health plan preferences component 276 supports both generic and branded drugs since health plans generally do. If a prescriber elects to search for allowed drug samples by health plan or otherwise restricts the search within therapeutic class to the drugs allowed by the health plan, only drugs allowed by the health plan will be returned as available samples. Additionally, if the health plan has a preferred set of drugs, the returned list of sample candidates will be organized to reflect this preference. If the sample leads to a prescription, this tight integration of sampling with health plan requirements will ensure the patient is covered for the prescription and thus greatly improves the efficiency of the process.

The electronic authorization and authentication component 278 provides the necessary support for analyzing and validating digital and digitized signatures. Whereas an electronic authorization and authentication is a cryptographic instrument which assures the identity of the person using it, a digitized signature is simply an image of a signature.

Fraud analysis component 280 is a set of metrics that identifies probable fraudulent sample redemptions. Identifying fraudulent sampling—diversions, copying coupons or e-vouchers, multiple samples to the same patient—is important both from the standpoint of proper return-on-investment computation and compliance with applicable law.

Inferential analysis component 282 provides a moving analysis of trend and profiling data. The promotional orchestration engine 234 can use the inferential analysis component 282 to continually upgrade services and target marketing to pharmas, fulfillment houses, and channels, and these agencies can use inferential data to more closely target marketing to the promotional orchestration engine users. For example, demographic, prescriber, and usage data can be combined to infer how to properly market to prescribers. When a prescriber begins practice, the prescriber serves a particular demographic based on the type of practice and patient demographics. This demographic changes over time: if a prescriber starts with a patient demographic that includes a lot of infants, it is predictable that in a few years the prescriber will have a practice with many children. If you know what sorts of drugs and services are used by prescribers with many children for patients, you can infer that a prescriber with many infant patients now will likely be interested in those services within a predictable timeframe. This means that at the appropriate time, the information pushed to the prescriber by the promotional orchestration engine and sales representatives can start to reflect the drugs used by prescribers with children rather than infants.

If sufficient information is collected about the prescriber and his prescribing habits from the usage component 268, enough demographic data about the prescriber from the prescriber profile, and enough demographic data from the Census or other sources about the prescriber's geographic area, the promotional orchestration engine 230 can generate a profile of a prescriber practice over time and what should be marketed to that practice at each stage. Similarly, inferential analysis can be used to allocate resources. Most marketing resources are concentrated on the top deciles of prescribers, i.e., prescribers who write a lot of prescriptions. However, this group does not remain constant. Ideally, a sales representative wants to know which prescribers in the top deciles are slowing down (so that additional incentives and/or fewer resources will be used for those prescribers) and which prescribers in lower deciles are likely to move into the top deciles. Again, the information in usage component 268 plus the prescriber profile data can be used to infer which prescribers fall into each category and therefore how best to expend sales rep resources.

Prescriber profiles 284 contain the basic demographic and professional information for the user. This information is generally not visible or modifiable by the user. It is used in the predictive profiling process for multivariate and trendline analysis, for construction of the profiles for the particular prescriber, and other statistical processing. Examples of prescriber profile information include age; gender; opinion leadership position; decile; decile by therapeutic class; sampling history; derived groups and market segments; geographic location; and specialties. Prescriber profiles are constantly updated, both by prescriber interaction with the promotional orchestration engine and by data swapping and collaboration with channels and data suppliers 236. Channels, particularly portal channels, gain insights into prescriber behavior by tracking prescriber activities on the channel's Web site or in the channel's services. Since the channel offers a different but related set of functions to the promotional orchestration engine, additional information can be gleaned by combining information from the channel with information from the promotional orchestration engine. The mechanism for doing this is the prescriber profile: data from channels is stored in the profile and analyzed in precisely the same fashion as native promotional orchestration engine data.

Figure 2F:
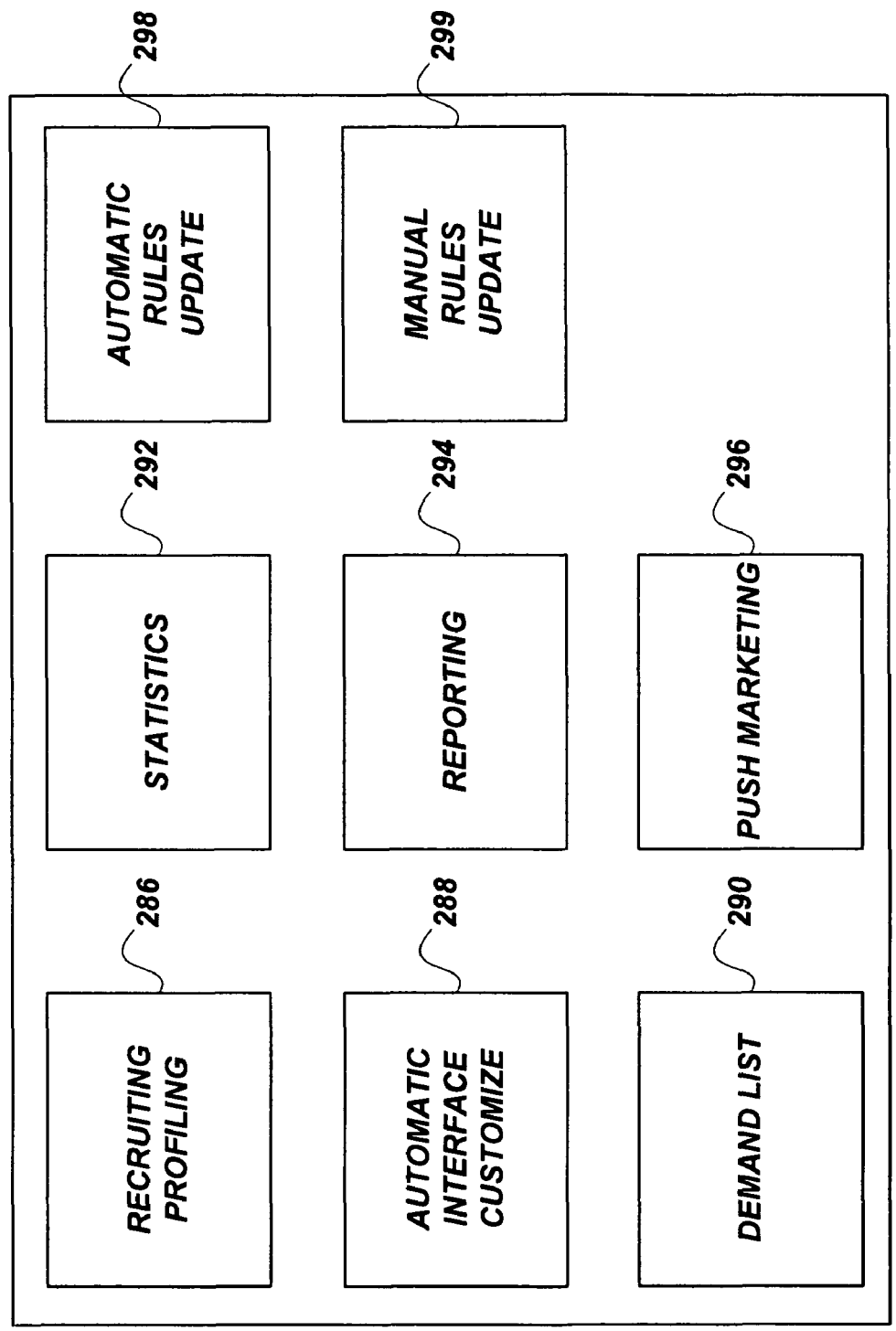
FIG. 2F is a block diagram illustrating pieces of a learning engine, according to one embodiment of the present invention.
Figure 3A:
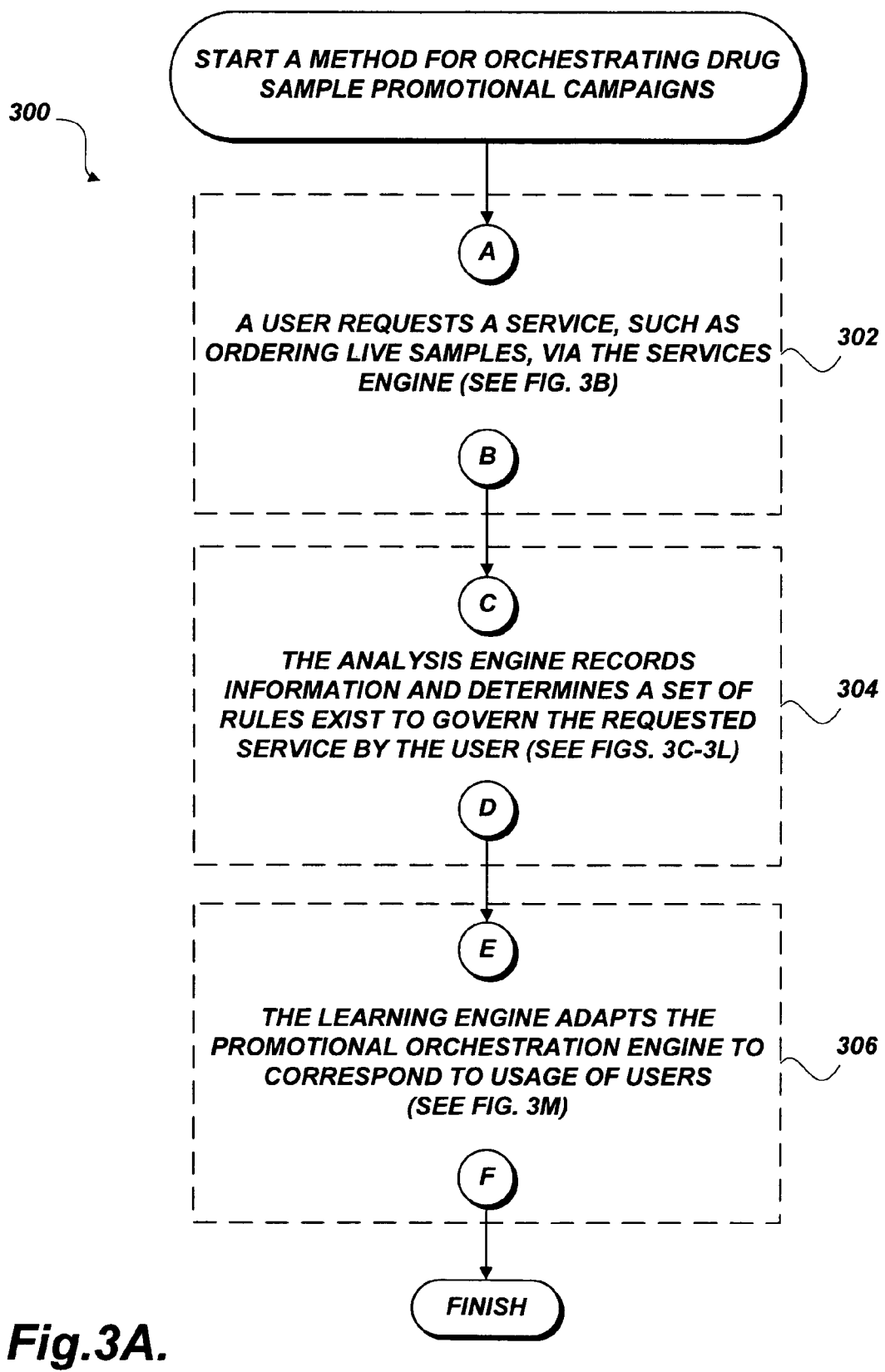
FIGS. 3A-3M are process diagrams illustrating a method for orchestrating drug sample promotional campaigns, according to one embodiment of the present invention.
Figure 3B:
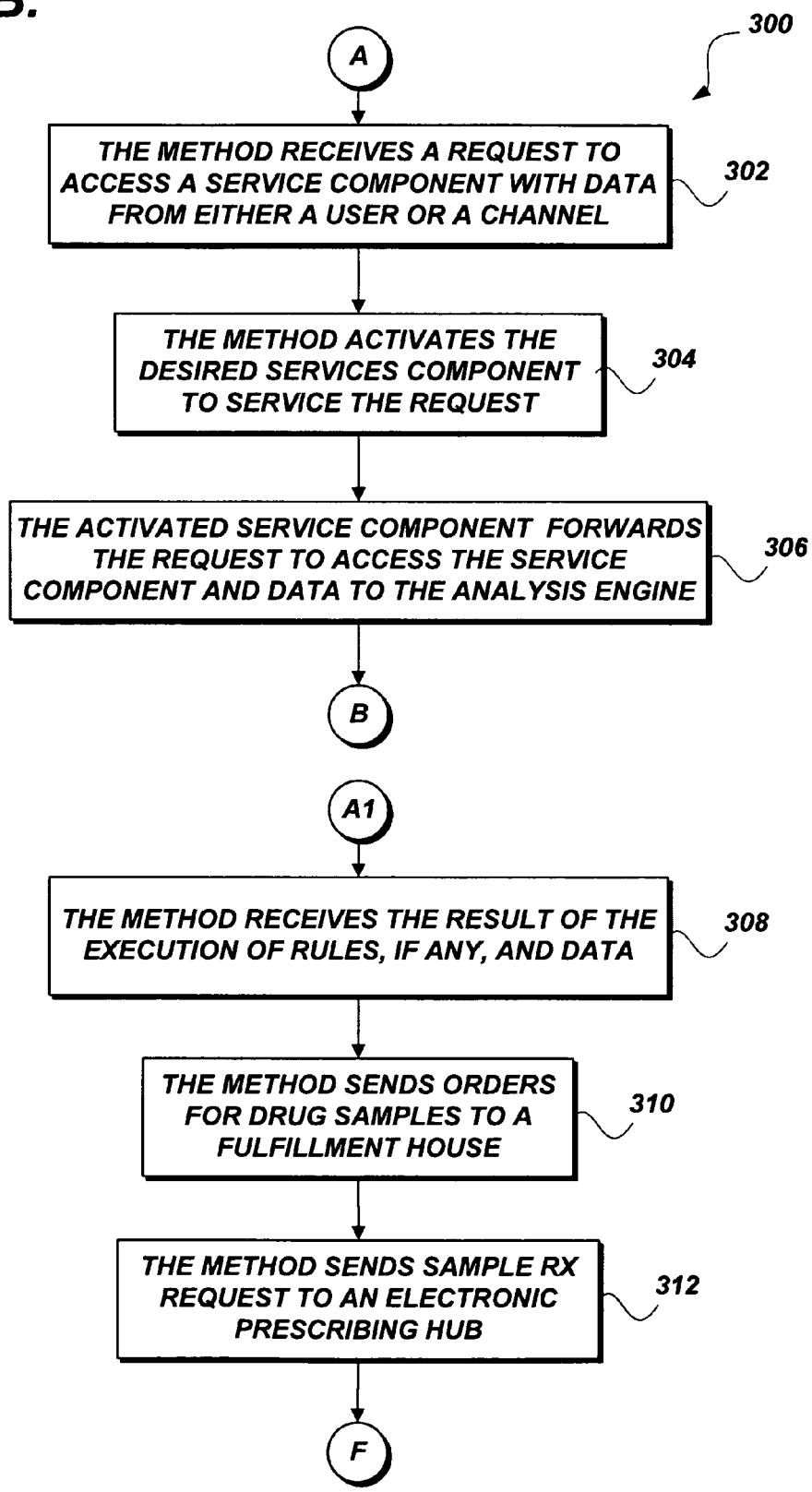
Figure 3C:
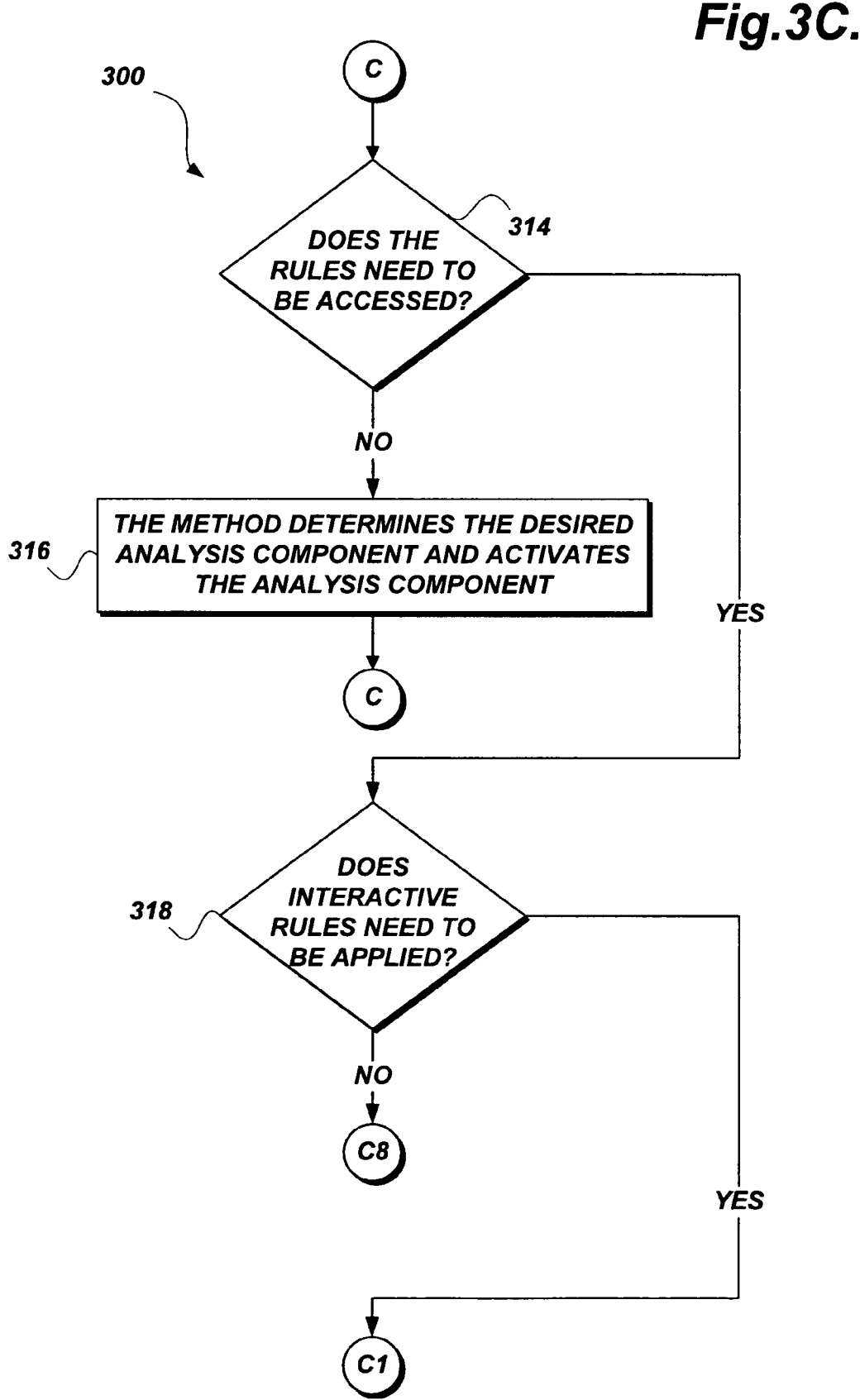
Figure 3D:
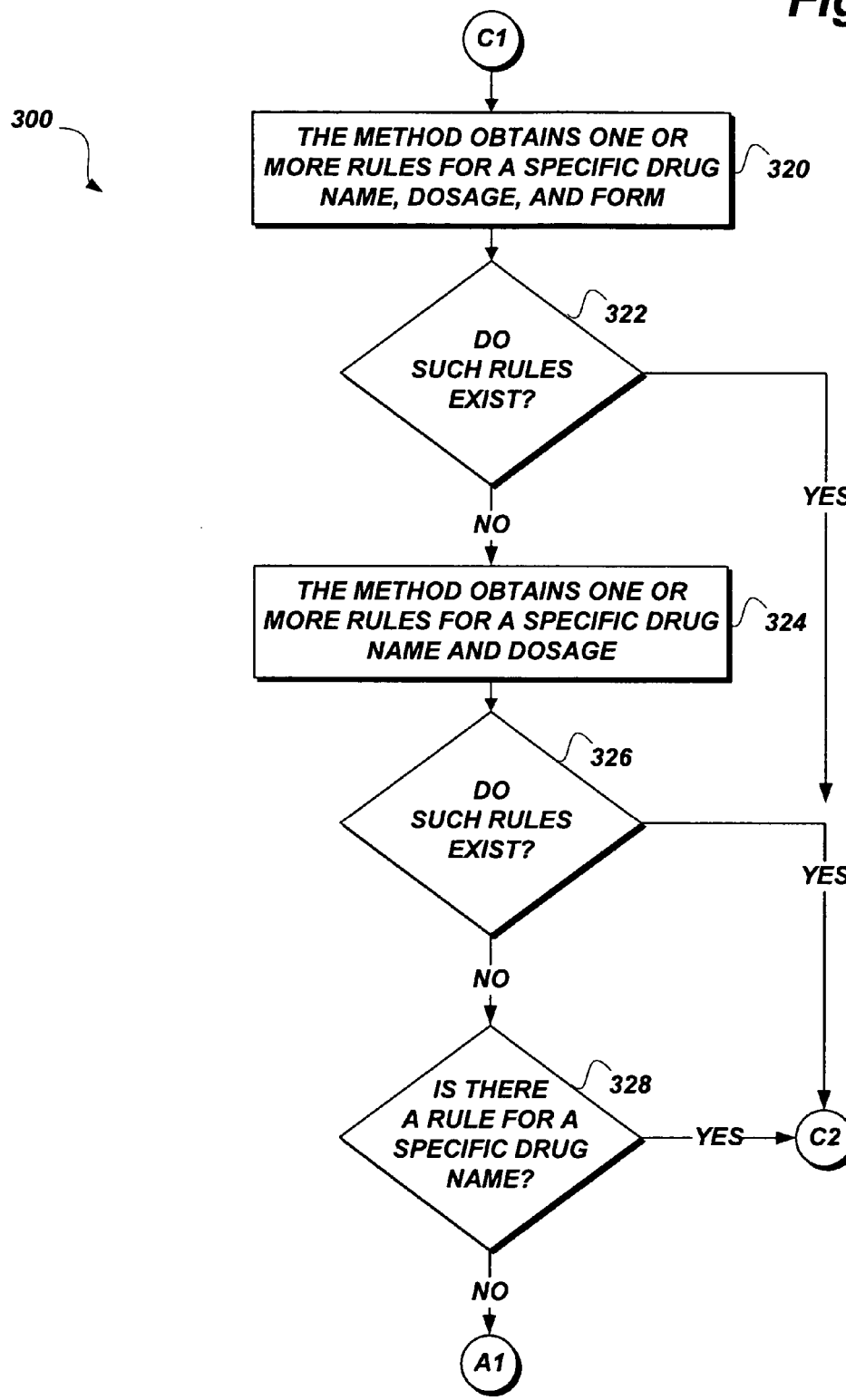
Figure 3E:
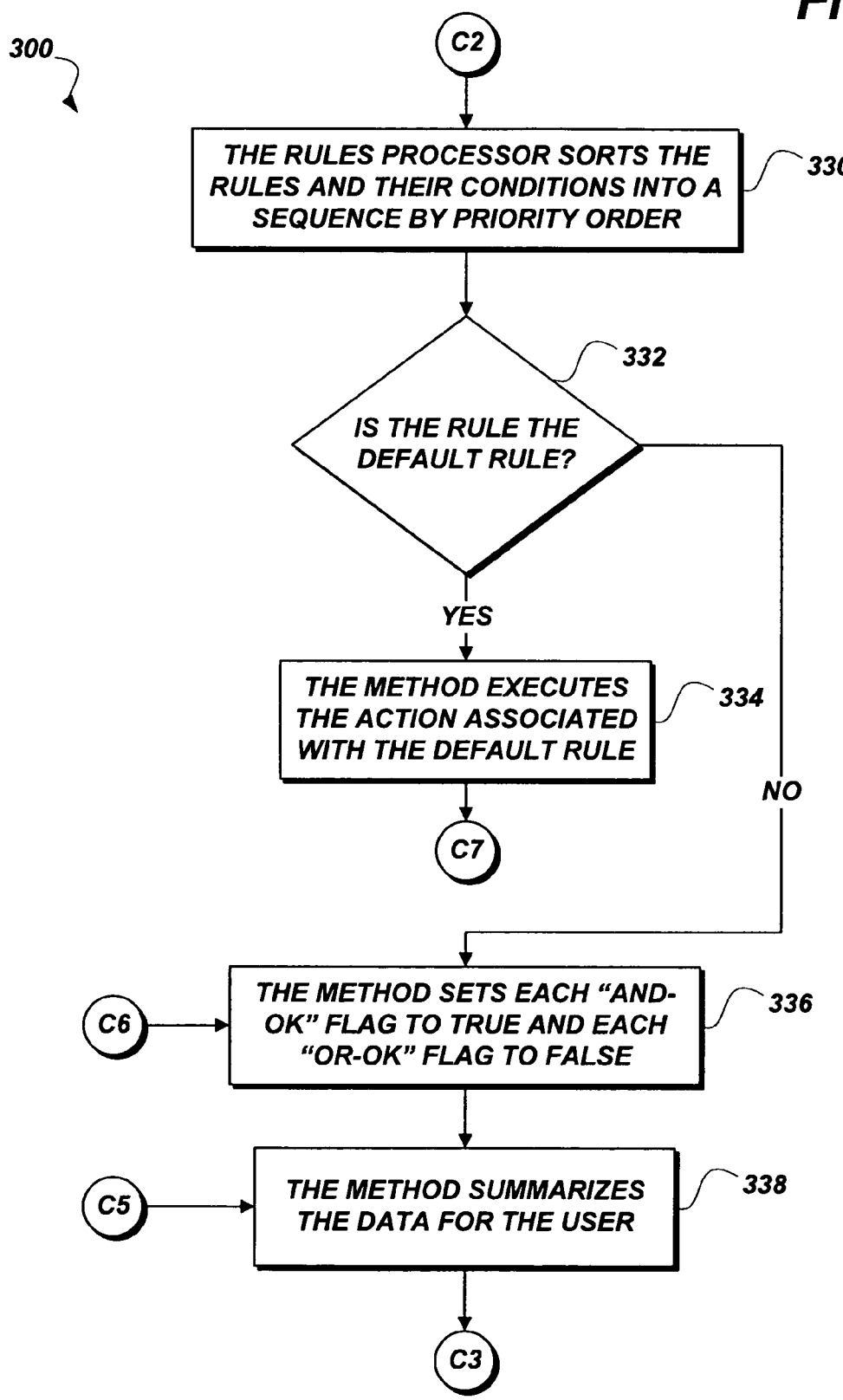
Figure 3F:
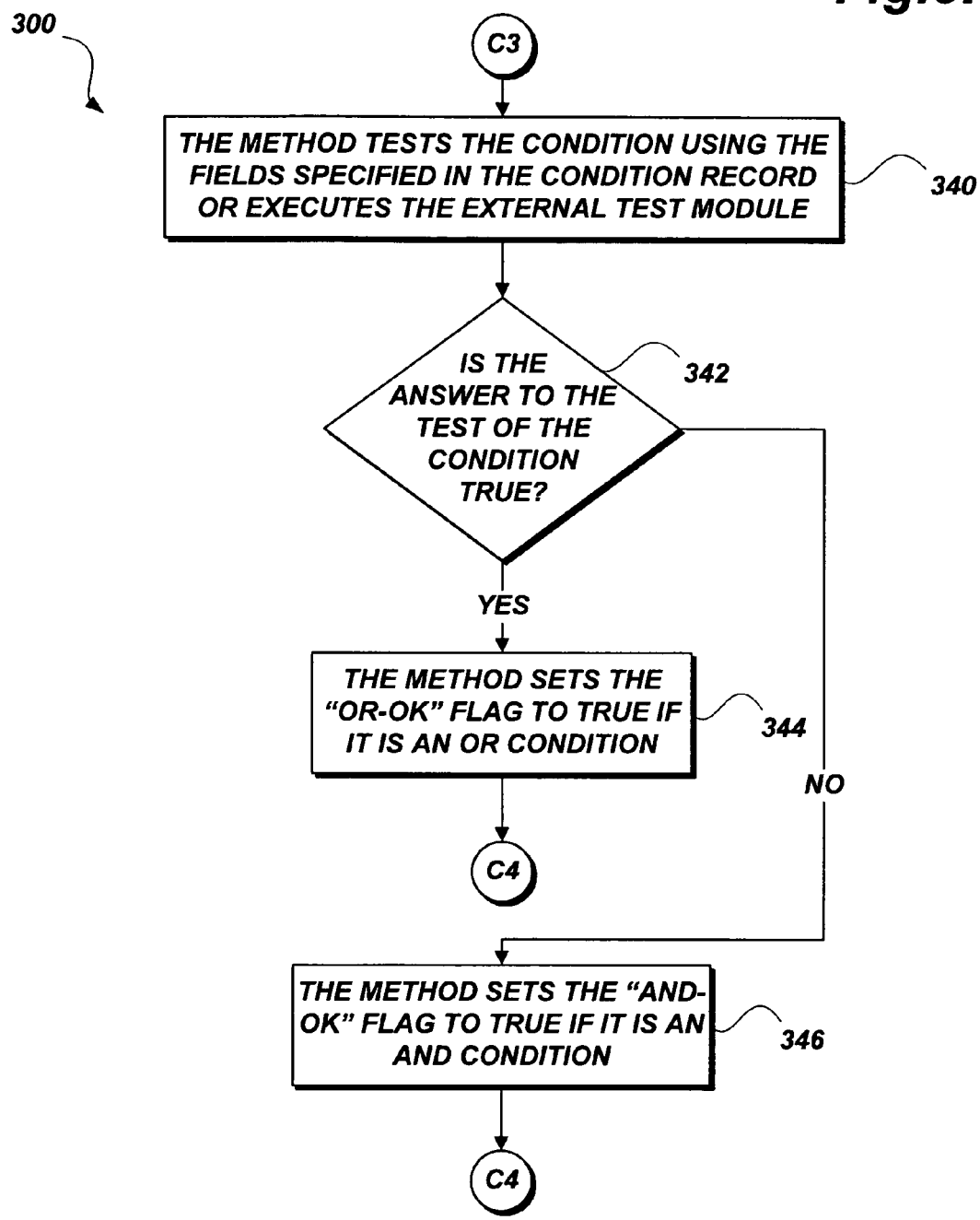
Figure 3G:
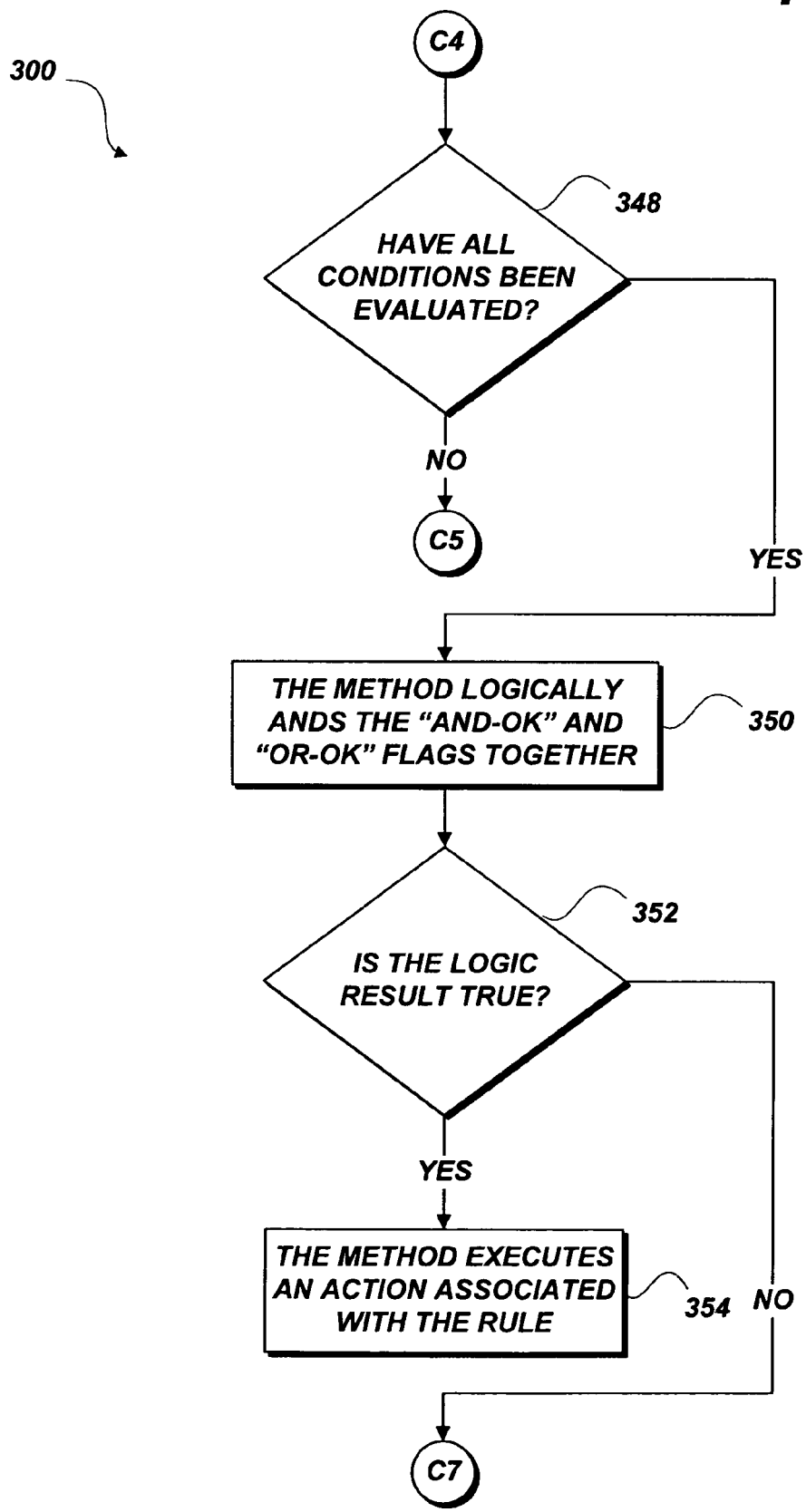
Figures 3H, 3I:
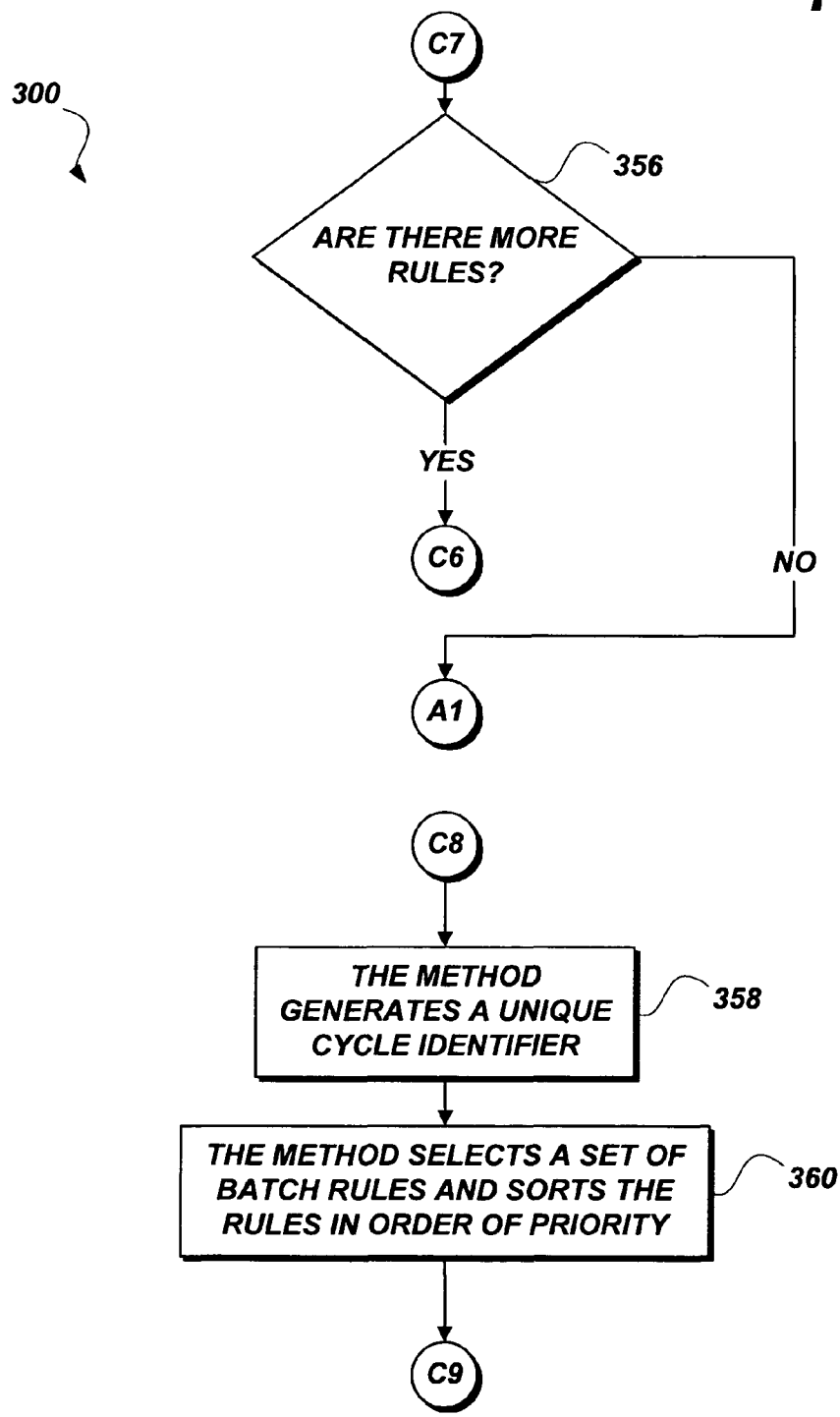
Figure 3J:
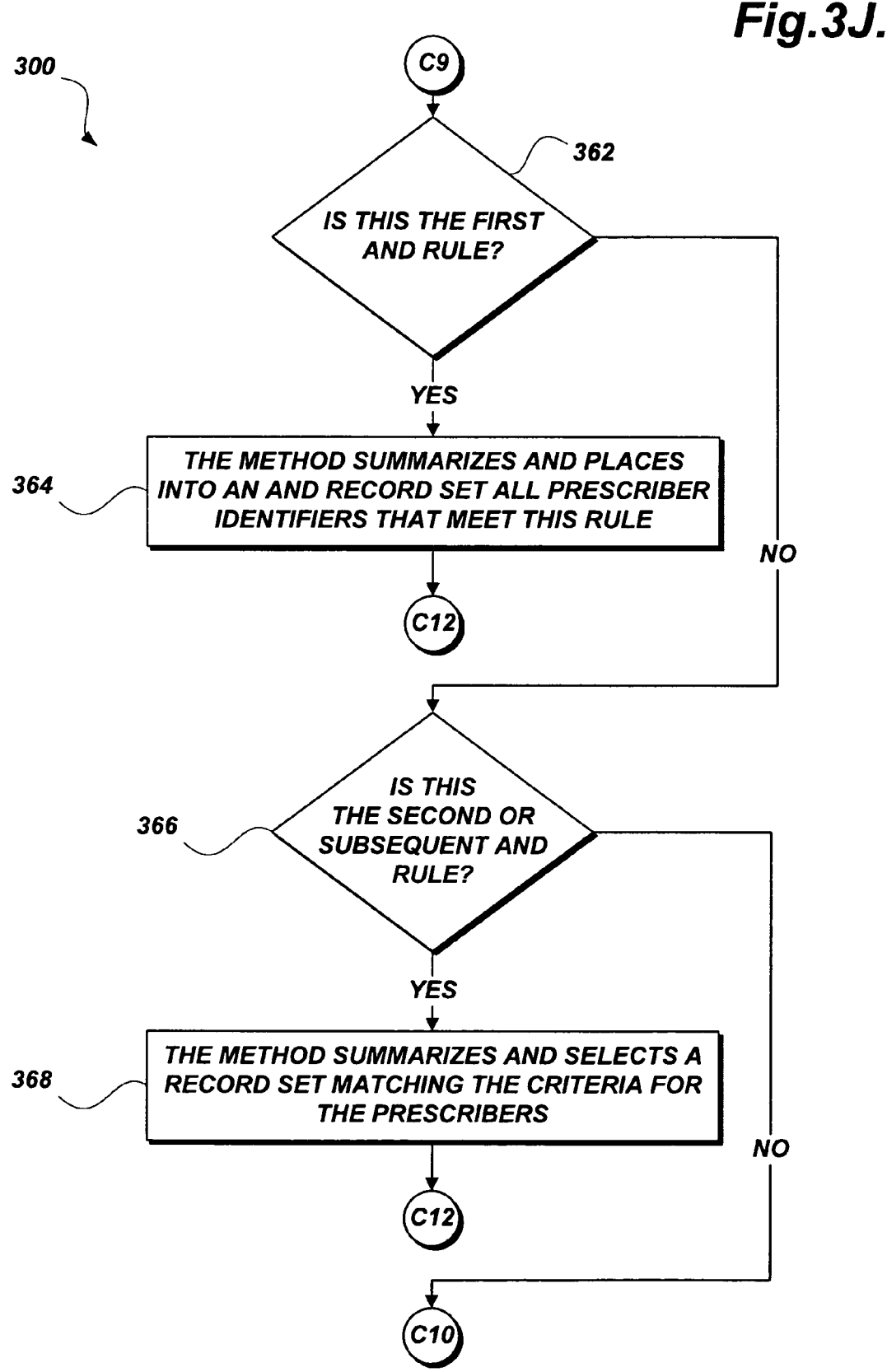
Figure 3K:
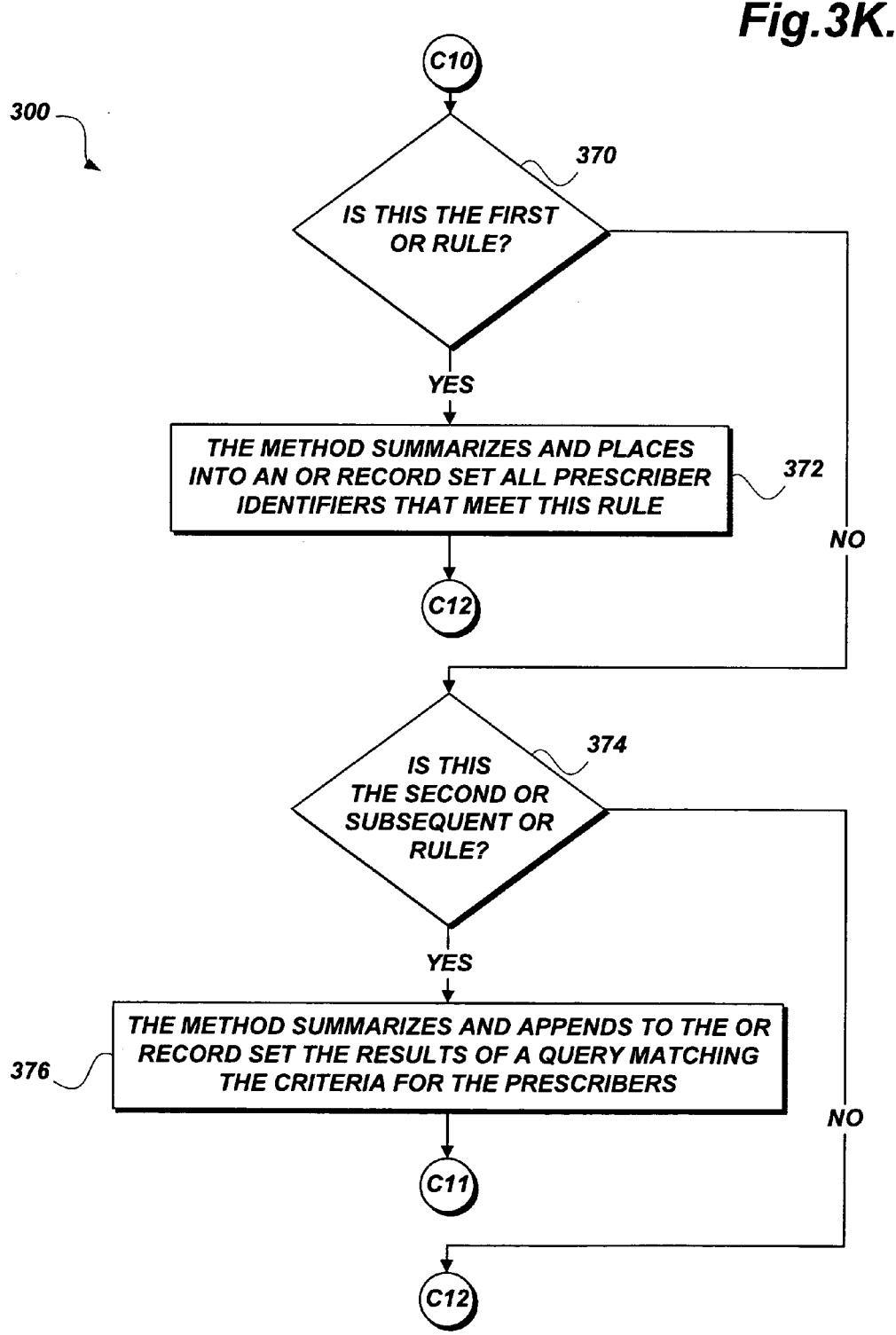
Figure 3L:
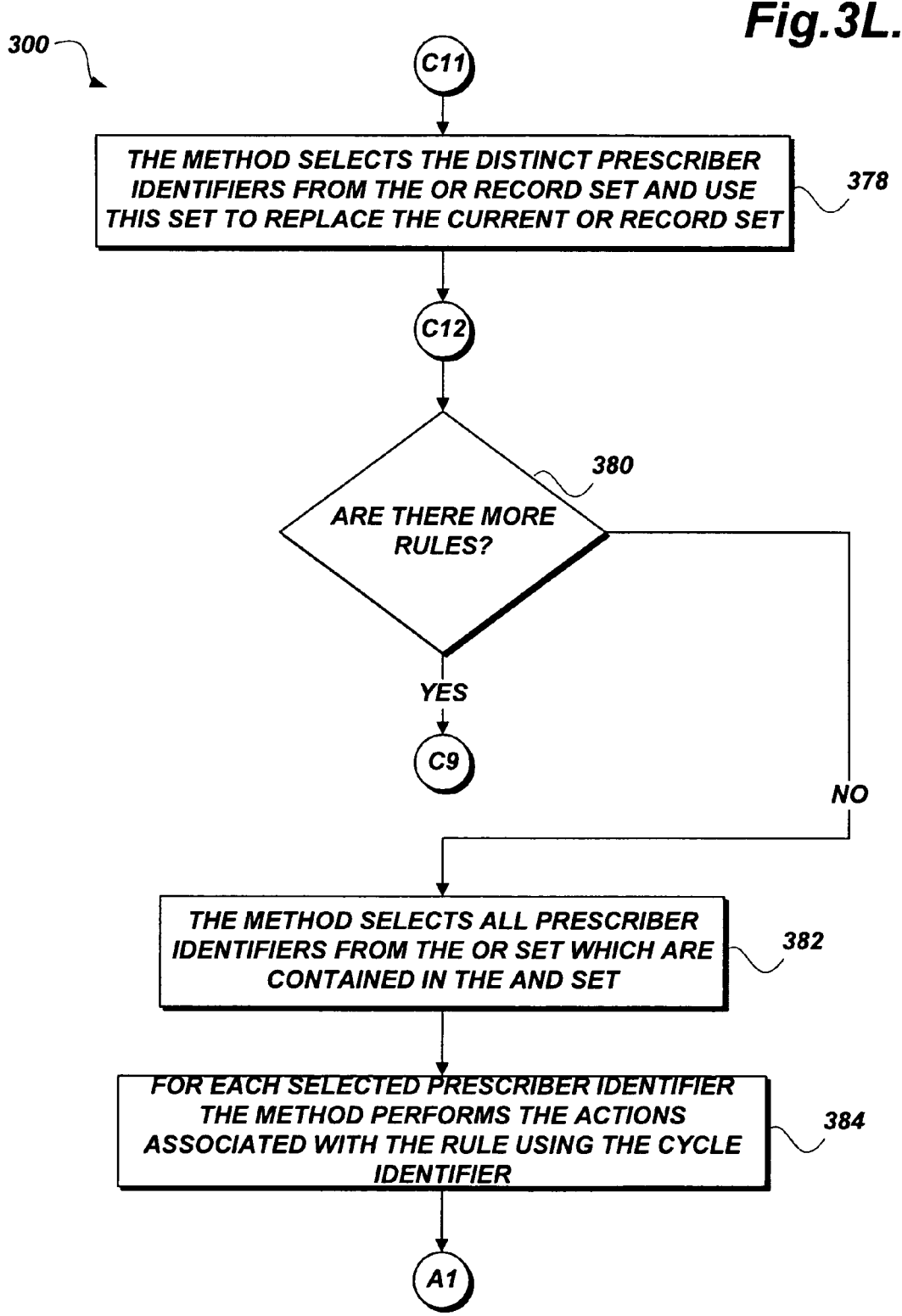
Figure 3M:
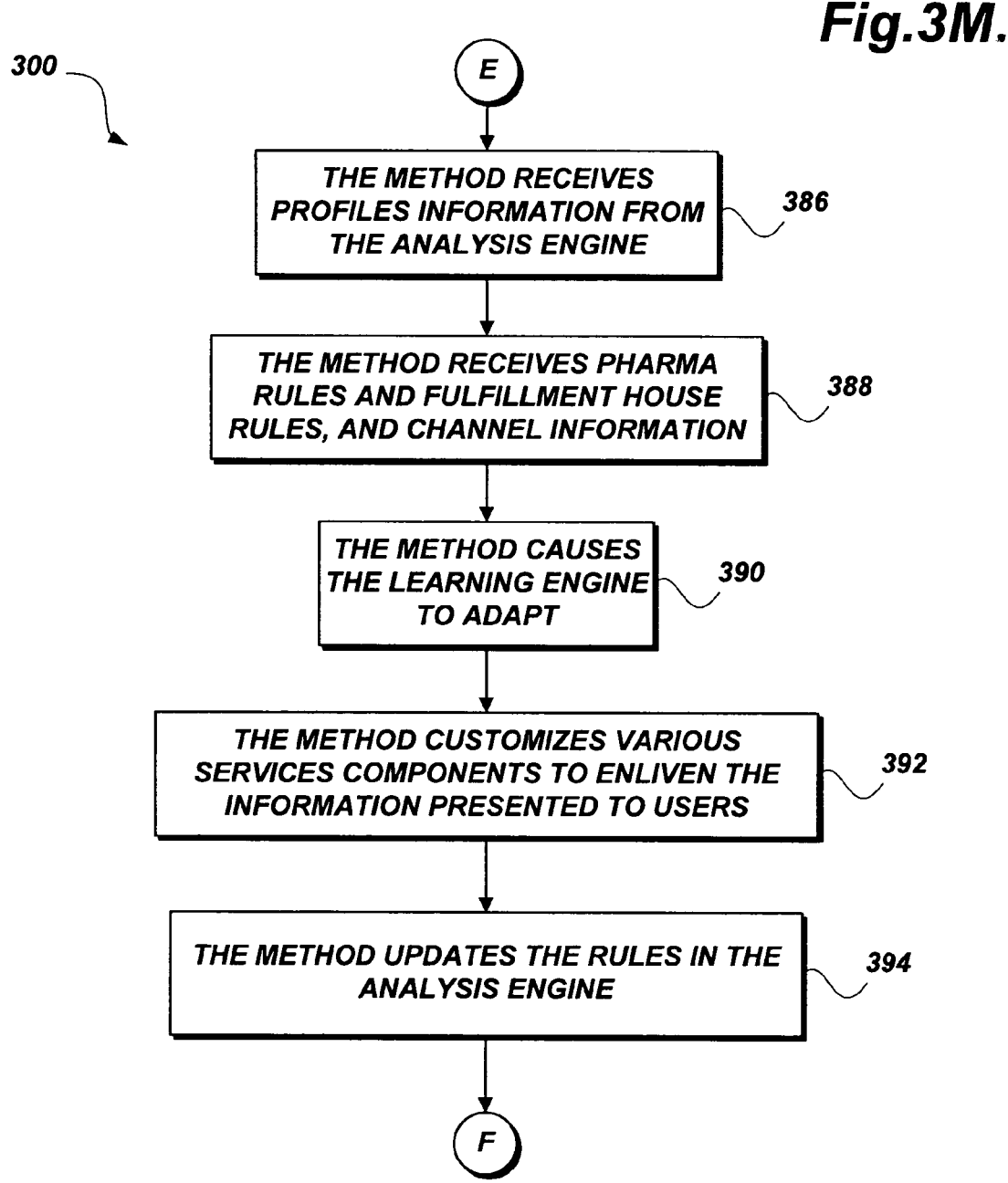

A key function of the promotional orchestration engine 230 is its ability to adapt over time to the users of the system and its own functions using the learning engine 236. See FIG. 2F. Many systems offer the ability for the user to customize settings; the promotional orchestration engine 230 offers that but additionally modifies its own behavior based upon what the user does.

Recruiting profiling component 286 allows the optimization of recruiting efforts. As pharma customers submit requests for recruiting of specific practice segments or demographics, it becomes possible to draw a profile of what sort of prescriber is desirable for certain types of drugs at certain stages of development. Once these profiles can be drawn, a marketing recruiting services can be offered to pharma already-registered prescribers who fit the profiles for new or other products pharma wishes to emphasize. In other words, the recruitment process itself informs the desirable characteristics and with this information prescriber groups can be suggested to a pharma instead of waiting to be asked by the pharma.

Recruiting profiling component 286 also feeds the recruiting services of the services engine 232. Because this function tracks what criteria were used for campaigns and how well recruits responded, it can be used to analyze proper recruiting strategies. For example, a user could view earlier campaigns by therapeutic class, demographic, geographic, specialization, and similar criteria and the results of those campaigns to decide on which basis the current campaign should be implemented. (Note: this is abstracted information: it does not include the specific sales collateral used by those campaigns unless the user is authorized to see them. The idea is to allow the user to pick the most promising recruit group but the actual elements of the campaign are provided by the user).

Automatic interface customization component 288 is a way of making the interface convenient for a user based on what that user has done and is allowed to do. Automatic interface customization would include such dynamic features as: moving commonly used services and product links closer to the front/top of the application; removing links to products or services the user is not allowed to access; adding services and products similar to the ones the user has already selected to the front of the application; and comparing the specific user profile against an "average" user profile for the specialty and adjusting the user interface to include information and drugs from the "average" profile. In short, automatic interface customization tries to adapt the interface to cover both what the user is currently doing and what the user is most likely to do in the future. In practice, much of the automated interface customization is preferably implemented via the rules processor.

The demand list component 290 is a learning engine tool by which users of the system indicates what drugs they want. While the promotional orchestration engine 230 is not limited in the number of drugs it can manage, pharmas will not necessarily be willing to use the promotional orchestration engine 230 without some evidence that doing so will provide benefits. The demand list is a simple measure of the desire on the part of core users for a particular drug and thus a potential indicator of how effective the promotional orchestration engine 230 would be in marketing that drug.

Statistics component 292 is included in the learning engine 236 to adjust statistics presented based on the amount of data available. For example, during the early stages of a product rollout, there may be so little data that p-tests are used in preference to the z-test used with larger amounts of data. Correlation statistics may be based on straight values, lagged values, or lagged moving averages based on the amount of data available to the system and the accuracy of the fitted curve. Many users are not trained mathematicians or statisticians. For this reason the promotional orchestration engine 230 itself must adapt to present the most appropriate statistics available in order to avoid misleading or misinforming the user. We anticipate the statistics engine will allow users to override the statistics function recommendations as long as the function provides a warning that doing so may give inaccurate results.

Reporting component 294 provides "smart" reporting tools which do more than simply work with a static set of data. These tools produce conventional reports but are also based on which reports the user accesses and how the user manipulates the information in the data warehouse to be able to "suggest" new reports to the user. For example, if the user requests a series of trendlines based on single products, the smart reporting system would then suggest a trendline based on multivariate analysis of the products in order to be able to determine the degree of cross-product correlation.

Push marketing component 296 parallels automatic interface customization. The services and products a user selects reveal personal preferences. The profile of the user compared against the profiles over time of other users reveal areas of probable future interest and fall-offs in areas of current interest. Combining these two makes it possible to custom-tailor marketing to a specific user while the ability to customize the interface makes it possible to deliver this marketing cost-effectively. The net effect is two-fold: authorized users are informed in a targeted and time-efficient way of new products and services that are likely of interest to them; authorized users whose use of a specific product has begun to fall off can be targeted for specialized marketing, e.g., additional education, incentives, etc.; as with other features of the learning engine 236, at least some of the push marketing functions are implemented through the rules processor.

Automatic rule updates component 298 can be based on a variety of factors. A rules engine of various embodiments of the present invention is capable of understanding min, max, trend, growth percentage, time periods, min/max per period, prescriber decile, prescriber conversion of sample to prescription rate, therapeutic class interchange (e.g., allowing unused samples in one class to be transferred to a more popular class) and similar behavior-based metrics.

Manual rules update component 299 is the interface by which pharma or fulfillment houses can control the rules component 272. Each pharma and fulfillment house has some level of control over how and to whom its samples are dispensed. This interface allows the pharma or fulfillment house to establish and maintain those rules. If the pharma or fulfillment house allows it, a rule initially set up using the manual rules update can be updated by the automatic rules update component 298. For example, a manual rule might say "a prescriber is allowed to dispense up to 10 samples of this drug in a 30-day period." This requires the pharma/fulfillment house to periodically review the rule to ensure quantities and time periods are current. On the other hand, the pharma/fulfillment house could set up an automatically updating rule that says "prescribers are allowed to dispense up to 20% more samples per 30-day period than in the prior 30 period subject to a maximum of 50 samples." The latter rule is dynamic: it adapts to prescriber behavior by allowing the prescriber to increase use of samples without explicitly requiring a manual rule update.

FIGS. 3A-3M illustrate a method 300 for orchestrating drug sample promotional campaigns. For clarity purposes, the following description of the method 300 makes references to various elements illustrated in connection with the promotional orchestration engine 230 (FIGS. 2B-2F). From a start block, the method 300 proceeds to a set of method steps 302, defined between a continuation terminal ("terminal A") and an exit terminal ("terminal B"). The set of method steps 302 describes that a user requests a service, such as ordering physical samples, via the services engine 232.

From terminal A (FIG. 3B), the method 300 proceeds to block 302 where the method receives a request to access a service component 238-260 with data from either a user 202-208 or a channel, such as channels 218. Next, at block 304, the method 300 activates the desired service component to service the request. The activated service component forwards the request to access the service component and data to the analysis engine 234. See block 306. The method 300 then enters the exit terminal B. From the exit terminal B (FIG. 3A), the method 300 proceeds to a set of method steps 304, defined between a continuation terminal ("terminal C") and an exit terminal ("terminal D"). The set of method steps 304 describes the ways in which the analysis engine records information and determines a set of rules exist to govern the requested service by the user.

From terminal C (FIG. 3C), the method 300 proceeds to decision block 314 where a test is made to determine whether the rules need to be accessed. If the answer is NO to the test at decision block 314, the method 300 proceeds to block 316 where the method 300 determines the desired analysis component and activates the analysis component. The method 300 then proceeds to the exit terminal C. If the answer to the test at decision block 314 is YES, another test is performed at decision block 318 to determine whether interactive rules need to be applied. If the answer to the test at decision block 318 is NO, the method 300 proceeds to another continuation terminal ("terminal C8"). Otherwise, the answer to the test at decision block 318 is YES, and the method 300 proceeds to yet another continuation terminal ("terminal C1").

From terminal C1 (FIG. 3D), the method 300 proceeds to block 320, where the method 300 obtains one or more rules for a specific drug name, dosage, and form. A test is performed at decision block 322 to determine whether such rules exist. If the answer is NO to the test at decision block 322, the method 300 obtains one or more rules for a specific drug name and dosage. See block 324. The method continues at decision block 326 where another test is performed to determine whether such rules exist. If the answer is also NO to the test at decision block 326, the method 300 progresses to decision block 328 where as yet another test is executed to determine whether there is a rule for a specific drug name. If the answer is NO to the test at decision block 328, the method proceeds to another continuation terminal ("terminal A1"). If the answer to the tests at decision blocks 322-328 is YES, the method 300 proceeds to another continuation terminal ("terminal C2").

From terminal A1 (FIG. 3B), the method 300 receives the results of the execution of rules, if any, and data. See block 308. At block 310, the method 300 sends orders for drug samples to a fulfillment house 228. The method 300 then sends a sample prescription request (electronic voucher) to an electronic prescribing hub. See block 312. The method 300 then continues to another continuation terminal ("terminal F"). From terminal F (FIG. 3A), the method 300 terminates execution.

From terminal C2 (FIG. 3E), the rules processor sorts the rules and their condition into a sequence by priority order. See block 330. The method 300 proceeds to decision block 332 where a test is performed to determine whether the rule is the default rule. If the answer to the test at decision block 332 is YES, the method 300 executes the action associated with the default rule. See block 334. The method 300 then continues to another continuation terminal ("terminal C7"). If the answer to the test at decision block 332 is NO, the method 300 sets each "AND-OK" flag to True and each "OR-OK" flagged to False. See block 336. The method 300 then summarizes the data for the user. See block 338. The method 300 then progresses toward another continuation terminal ("terminal C3").

From terminal C3 (FIG. 3F), the method 300 tests the condition using the fields specified in the condition record or executes the external test module. See block 340. A test is performed at decision block 342 to determine whether the answer to the test of the condition is True. If the answer is YES, the method 300 sets the "OR-OK" flag to True if it is an OR condition. See block 344. The method 300 proceeds then to another continuation terminal ("terminal C4"). If the answer to the test at decision block 342 is NO, the method 300 sets the "AND-OK" flag to true if it is an AND condition. See block 346. The method 300 then continues to terminal C4.

From terminal C4 (FIG. 3G), the method 300 proceeds to decision block 348 where a test is performed to determine whether all conditions have been evaluated. If the answer is NO to the test at decision block 348, another continuation terminal ("terminal C5") is entered by the method 300. From terminal C5 (FIG. 3E), the method 300 loops back to block 338 where the above-described processing steps are repeated. Otherwise, the answer to the test at decision block 348 is YES, and the method 300 logically ends the "AND-OK" and "OR-OK" flags together. See block 350. The method 300 then proceeds to decision block 352 where a test is performed to determine whether the logic result is True. If the answer to the test at decision block 352 is YES, the method 300 executes an action associated with a rule. See block 354. If the answer to the test at decision block 352 is NO, the method 300 continues at another continuation terminal ("terminal C7").

From terminal C7 (FIG. 3H), the method 300 proceeds to decision block 356 where a test is made to determine whether there are more rules to evaluate. If the answer is YES, the method continues to another continuation terminal ("terminal C6"). From terminal C6 (FIG. 3E), the method 300 loops back to block 336 where the above-described processing steps are repeated. If the answer to the test at decision block 356 is NO, the method 300 continues to terminal A1 where the method loops back to block 308 and the above-described processing steps are repeated. From terminal C8 (FIG. 3I), the method generates a unique cycle identifier. See block 358. The method 300 then selects a set of batch rules and sorts the rules in order of priority. See block 360. The method 300 then continues at another continuation terminal ("terminal C9").

From terminal C9 (FIG. 3J), the method 300 proceeds to decision block 362 to perform a test and determine whether this rule is the first END rule. If the answer to decision block 362 is YES, the method 300 summarizes and places into an END record set all prescriber identifiers that meet this rule. See block 364. The method 300 then continues at another continuation terminal ("terminal C12"). If the answer to the test at decision block 362 is NO, the method 300 proceeds to another decision block where another test is performed to determine whether this rule is the second or subsequent END rule. If the answer is YES to the test at decision block 366, the method 300 summarizes and selects a record set matching the criteria for the prescribers. See block 368. The method 300 then continues to terminal C12. If the answer to the test at decision block 366 is NO, the method 300 proceeds to another continuation terminal ("terminal C10").

From terminal C10 (FIG. 3K), the method 300 continues to decision block 370 where a test is made to determine whether it is the first OR rule. If the answer is YES to the test at decision block 370, the method 300 summarizes and places into an OR record set all prescriber identifiers that meet this rule. See block 372. The method progresses to terminal C12. If the answer to the test at decision block 370 is NO, the method 300 determines whether it is the second or subsequent OR rule. See decision block 374. If the answer is YES, the method 300 summarizes and appends to the OR record set the results of a query matching the criteria for the prescribers. See block 376. Otherwise, the answer to the test at decision block 374 is NO, and the method 300 continues to terminal C12.

From terminal C11 (FIG. 3L), the method 300 selects the distinct prescriber identifiers from the OR record set and uses the set to replace the current OR record set. See block 378. The method 300 continues to terminal C12, which flows to decision block 380 where a test is made to determine whether there are more rules. If the answer to the test at decision block 380 is YES, the method 300 proceeds to terminal C9 where it loops back to decision block 362 and the above-described processing steps are repeated. If the answer to the test at decision block 380 is NO, the method 300 selects all prescriber identifiers from the OR set which are contained in the AND set. See block 382. For each selected prescriber identifier, the method performs the actions associated with the rule using the cycle identifier. See block 384. The method 300 proceeds to terminal A1 to loop back to block 308 where the above-described processing steps are repeated.

From terminal D, the method 300 proceeds to a set of method steps 306 defined between a continuation terminal ("terminal E") and the terminal F. The set of method steps 306 describes the process by which the learning engine adapts the promotional orchestration engine to correspond to usage of users.

From terminal E (FIG. 3M), the method 300 receives profile information from the analysis engine 234. See block 386. The method 300 receives pharma rules and fulfillment house rules, and channel information. See block 388. The method 300 causes the learning engine to adapt. See block 390. At block 390, the method 300 preferably executes steps 358 (FIG. 3I) to step 384 (FIG. 3L) so as to adapt the promotional orchestration engine 230. The method 300 then customizes various services components 238-260 to enliven the information presented to users. See block 392. The method 300 then updates the rules in the analysis engine 234. See block 394. The method 300 then continues to terminal F, where it terminates execution.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for orchestrating drug sample distribution, comprising:
   a services engine being executed on a piece of hardware for fulfilling transaction requests by a prescriber to access services;
   an analysis engine being executed on the piece of hardware or another piece of hardware for executing a set of rules associated with a service requested by the prescriber, the set of rules defining whether the prescriber can receive a particular drug sample, its dosage, and its form; and
   a learning engine being executed on the piece of hardware or another piece of hardware and being configured to execute software steps so that the services in the services engine and the set of rules in the analysis engine customize information associated with services accessed by the prescriber, which information appears as if it were personalized to the prescriber, the learning engine determining whether the prescriber receives services corresponding to the requested service comprising certain types of drugs at certain stages of development including after development, based on one or more behaviors selected from a group consisting essentially of one or more samples requested by the prescriber in a given period of time, whether the prescriber has had mandatory education, and whether the prescriber accepts a visit from a pharmaceutical representative.

2. The system of claim 1, wherein the services engine includes an inventory management service for managing a computer-implemented drug closet.

3. The system of claim 1, wherein the services engine includes a representative visit scheduling service that allows the prescriber to request a visit from a sales representative.

4. The system of claim 1, wherein the services engine includes a physical samples, vouchers, and e-coupons service for authorizing the prescriber to provide drug samples to patients.

5. The system of claim 1, wherein the services engine includes an e-learning link service to provide on-line education regarding a particular therapeutic drug.

6. The system of claim 1, wherein the services engine includes patient assistance service to facilitate drug programs for indigent or low-income patients.

7. The system of claim 1, wherein the services engine includes pre-enroll services to enroll a number of prescribers to the system at once.

8. The system of claim 1, wherein the services engine includes representative services to assist sales representatives with planning sales visits with the prescriber.

9. The system of claim 1, wherein the services engine includes pharma services for reporting trends and behaviors of the prescriber to the pharma.

10. The system of claim 1, wherein the services engine includes a knowledge base service for allowing the prescriber to search for medical information.

11. The system of claim 1, wherein the services engine includes a personalization/customization service for allowing the prescriber to customize a service that he is using.

12. The system of claim 1, wherein the services engine includes a patient education service that allows the patient to access education material regarding how to begin a drug regimen by printing such material or receiving it via common carrier delivery.

13. The system of claim 1, wherein the services engine includes recruiting services that allow a pharmaceutical company to initiate a recruiting campaign to attract prescribers to prescribe a drug.

14. The system of claim 1, wherein the analysis engine includes a usage component for tracking sampling activities of the prescriber.

15. The system of claim 1, wherein the analysis engine includes a samples vs. prescription component for correlating drug sampling activities to prescribing behavior.

16. The system of claim 1, wherein the analysis engine includes a rules component for containing the set of rules, the rules component executing the set of rules to determine whether the service requested by the prescriber is accessible.

17. The system of claim 1, wherein the analysis engine includes a prescriber preferences component for tracking preferences of the prescriber in using the system.

18. The system of claim 1, wherein the analysis engine includes a health plan preferences component for tracking the drug preferences of a health plan.

19. The system of claim 1, wherein the analysis engine includes a electronic authorization and authentication component for analyzing and validating electronic, digital and/or digitized signatures.

20. The system of claim 1, wherein the analysis engine includes a fraud analysis component for identifying fraudulent sampling.

21. The system of claim 1, wherein the analysis engine includes an inferential analysis component for providing analysis of trend and profiling data.

22. The system of claim 1, wherein the analysis engine includes a prescriber profiles component for providing demographic and professional information regarding the prescriber.

23. The system of claim 1, wherein the learning engine includes a recruiting profiling component for optimization of the process of recruiting prescribers for drug sampling.

24. The system of claim 1, wherein the learning engine includes an automatic interface customization component for customizing a user interface based on what the prescriber has done and is allowed to do.

25. The system of claim 1, wherein the learning engine includes a demand list component that tracks the desire of prescribers for a certain drug.

26. The system of claim 1, wherein the learning engine includes a statistics component that adjust statistics based on the amount of data that is available.

27. The system of claim 1, wherein the learning engine includes a reporting component that provides reports to the pharmaceutical customer.

28. The system of claim 1, wherein the learning engine includes a push marketing component that customizes a marketing campaign to prescribers.

29. The system of claim 1, wherein the learning engine includes an automatic rules update component for updating the set of rules.

30. The system of claim 1, wherein the learning engine includes a manual rules update component for providing an interface through which a pharma can control changes to the set of rules.

31. A method for orchestrating a drug sample promotional campaign, comprising:
receiving, by a computer or another computer, a request by a user to access a service that includes a software drug closet;
recording the request by an analysis engine executing on the computer or another computer, the analysis engine determining a set of rules for governing the service as requested by the user, which allows the user to prescribe drug samples that are placed in the software drug closet;
adapting a promotional orchestration engine executing on the computer or another computer to respond to the behaviors and preferences of the user by displaying a user interface to a display coupled to the computer which is responsive to the behaviors and preferences of the user by selectively replenishing the drug samples in the software drug closet, ; and
determining whether the prescriber receives services corresponding to the requested service comprising certain types of drugs at certain stages of development including after development, based on one or more behaviors selected from a group consisting essentially of one or more samples requested by the prescriber in a given period of time, whether the prescriber has had mandatory education, and whether the prescriber accepts a visit from a pharmaceutical representative.

32. The method of claim 31, wherein the act of determining includes determining the set of rules as interactive rules when the request is by a prescriber for samples or e-samples.

33. The method of claim 32, wherein the act of determining the set of rules as interactive rules returns a quantity of allowable number of drug samples as a response to the request by the prescriber.

34. The method of claim 31, wherein the act of determining includes determining the set of rules as batch rules when an interval of time has expired.

35. The method of claim 34, wherein the act of determining the set of rules as batch rules customizes a user interface based on the behaviors and preferences of the prescriber.

36. A non-transitory computer-readable medium having computer-executable instructions stored there on for performing a method of orchestrating a drug sample promotional campaign, the method comprising:
receiving a request by a user to access a service that includes a computer-implemented drug closet;
recording the request by an analysis engine, the analysis engine determining a set of rules for governing the service as requested by the user, which allows the user to prescribe drug samples that are present in the computer-implemented drug closet;
adapting a promotional orchestration engine to respond to the behaviors and preferences of the user by selectively replenishing the drug samples in the computer-implemented drug closet; and
determining whether the prescriber receives services corresponding to the requested service comprising certain types of drugs at certain stages of development including after development, based on one or more behaviors selected from a group consisting essentially of one or more samples requested by the prescriber in a given period of time, whether the prescriber has had mandatory education, and whether the prescriber accepts a visit from a pharmaceutical representative.

37. The computer-readable medium of claim 36, wherein the act of determining includes determining the set of rules as interactive rules when the request is by a prescriber for samples or e-samples.

38. The computer-readable medium of claim 37, wherein the act of determining the set of rules as interactive rules returns a quantity of allowable number of drug samples as a response to the request by the prescriber.

39. The computer-readable medium of claim 36, wherein the act of determining includes determining the set of rules as batch rules when an interval of time has expired.

40. The computer-readable medium of claim 39, wherein the act of determining the set of rules as batch rules customizes a user interface based on the behaviors and preferences of the prescriber.

* * * * *